(12) United States Patent
Chandrakumar et al.

(10) Patent No.: US 10,778,165 B2
(45) Date of Patent: Sep. 15, 2020

(54) HIGH DYNAMIC RANGE SENSING FRONT-END FOR NEURAL SIGNAL RECORDING SYSTEMS

(71) Applicant: The Regents of the University of California, Oakland, CA (US)

(72) Inventors: Hariprasad Chandrakumar, Los Angeles, CA (US); Dejan Markovic, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 417 days.

(21) Appl. No.: 15/515,562

(22) PCT Filed: Sep. 30, 2015

(86) PCT No.: PCT/US2015/053336
§ 371 (c)(1),
(2) Date: Mar. 29, 2017

(87) PCT Pub. No.: WO2016/054274
PCT Pub. Date: Apr. 7, 2016

(65) Prior Publication Data
US 2017/0230019 A1 Aug. 10, 2017

Related U.S. Application Data

(60) Provisional application No. 62/058,017, filed on Sep. 30, 2014.

(51) Int. Cl.
*H03F 3/45* (2006.01)
*A61B 5/00* (2006.01)
(Continued)

(52) U.S. Cl.
CPC ..... *H03F 3/45475* (2013.01); *A61B 5/04004* (2013.01); *A61B 5/7203* (2013.01);
(Continued)

(58) Field of Classification Search
CPC ............ H03F 3/45475; A61B 5/04004; A61B 5/7203; A61B 5/7207
See application file for complete search history.

(56) References Cited

U.S. PATENT DOCUMENTS

5,633,989 A 5/1997 Shin et al.
5,847,601 A 12/1998 Wang
(Continued)

FOREIGN PATENT DOCUMENTS

EP 3202033 A1 8/2017
JP H06197877 A 7/1994
(Continued)

OTHER PUBLICATIONS

Extended European Search Report for European Application No. 15847435.3, Search completed Apr. 20, 2018, dated Jan. 30, 2019, 11 Pgs.
(Continued)

*Primary Examiner* — John R Downey
(74) *Attorney, Agent, or Firm* — KPPB LLP

(57) ABSTRACT

A high dynamic range sensing front-end for bio-signal recording systems in accordance with embodiments of the invention are disclosed. In one embodiment, a bio-signal amplifier includes an input signal, where the input signal is modulated to a predetermined chopping frequency, a first amplifier stage, a parallel-RC circuit connected to the first amplifier stage and configured to generate a parallel-RC circuit output by selectively blocking an offset current, a second amplifier stage connected to the parallel-RC circuit that includes a second input configured to receive the parallel-RC circuit output and generate a second output that is an amplified version of the input signal with ripple-rejection. Further, the bio-signal amplifier can also include an auxiliary path configured for boosting input impedance by pre-charging at least one input capacitor. In addition, the (Continued)

bio-signal amplifier can also include a DC-servo feedback loop that includes an integrator that utilizes a duty-cycled resistor.

16 Claims, 23 Drawing Sheets

(51) Int. Cl.
    *A61B 5/04*     (2006.01)
    *H03F 3/387*     (2006.01)
    *H03M 1/48*     (2006.01)

(52) U.S. Cl.
    CPC ............ *A61B 5/725* (2013.01); *A61B 5/7207* (2013.01); *A61B 5/7225* (2013.01); *H03F 3/387* (2013.01); *H03F 3/45744* (2013.01); *H03F 2200/168* (2013.01); *H03F 2200/261* (2013.01); *H03F 2200/459* (2013.01); *H03F 2203/45* (2013.01); *H03F 2203/45514* (2013.01); *H03M 1/48* (2013.01)

(56) References Cited

U.S. PATENT DOCUMENTS

| | | | |
|---|---|---|---|
| 6,456,159 B1 | 9/2002 | Brewer | |
| 7,132,883 B2 | 11/2006 | Huijsing et al. | |
| 7,696,817 B1 | 4/2010 | Boucher et al. | |
| 7,724,080 B2 * | 5/2010 | Luff | H03F 3/393 327/124 |
| 8,786,363 B2 * | 7/2014 | Ahmad | H03F 3/387 330/69 |
| 9,912,309 B1 * | 3/2018 | Ecker | H03F 3/393 |
| 10,003,306 B1 * | 6/2018 | Larson | H03F 1/26 |
| 2006/0189881 A1 | 8/2006 | Fassio | |
| 2008/0106330 A1 | 5/2008 | Yoshida et al. | |
| 2008/0269631 A1 | 10/2008 | Denison et al. | |
| 2009/0082829 A1 | 3/2009 | Panken et al. | |
| 2009/0309653 A1 * | 12/2009 | Luff | H03F 3/393 330/9 |
| 2010/0033240 A1 * | 2/2010 | Denison | A61B 5/0002 330/9 |
| 2012/0188009 A1 | 7/2012 | Alexander et al. | |
| 2013/0303942 A1 | 11/2013 | Damaser et al. | |
| 2013/0335141 A1 * | 12/2013 | Ahmad | H03F 3/387 330/69 |
| 2016/0294331 A1 * | 10/2016 | Ivanov | H03F 1/26 |
| 2020/0099352 A1 | 3/2020 | Chandrakumar et al. | |

FOREIGN PATENT DOCUMENTS

| | | |
|---|---|---|
| WO | 2014087980 A1 | 6/2014 |
| WO | 2016054274 A1 | 4/2016 |
| WO | 2018106877 A1 | 6/2018 |

OTHER PUBLICATIONS

International Preliminary Report on Patentability for International Application PCT/US2015/053336, Report issued Apr. 4, 2017, dated Apr. 13, 2017, 6 Pgs.
International Preliminary Report on Patentability for International Application PCT/US2017/065039, Report issued Jun. 11, 2019, dated Jun. 20, 2019, 5 Pgs.
International Search Report and Written Opinion for International Application No. PCT/US2015/053336, Search completed Jan. 13, 2016, dated Jan. 13, 2016, 8 Pgs.
International Search Report and Written Opinion for International Application No. PCT/US2017/065039, Search completed Feb. 12, 2018, dated Mar. 6, 2018, 14 Pgs.
Partial Supplementary European Search Report for European Application No. 15847435.3, Search completed Apr. 20, 2018, dated Oct. 26, 2018, 13 Pgs.
Belloni et al., "Low-Power Ripple-Free Chopper Amplifier with Correlated Double Sampling De-Chopping", IEEE International Symposium on Circuits and Systems (ISCAS), May 30-Jun. 2, 2010, Paris, France, pp. 765-768, DOI: 10.1109/ISCAS.2010.5537462.
Denison et al., "A2 µw 100 nV/rtHz Chopper-Stabilized Instrumentation Amplifier for Chronic Measurement of Neural Field Potentials", IEEE Journal of Solid-State Circuits, Dec. 1, 2007, vol. 42, No. 12, pp. 2934-2945.
Jochum et al., "Integrated circuit amplifiers for multi-electrode intracortical recording", Journal of Neural Engineering, Jan. 12, 2009, vol. 6, No. 1, 26 pgs.
Zhang et al., "Design of Ultra-Low Power Biopotential Amplifiers for Biosignal Acquisition Applications", IEEE Transactions on Biomedical Circuits and Systems, vol. 6, No. 4, Aug. 2012, pp. 344-355.
Akita et al., "A 0.06mm2 14nV/√Hz chopper instrumentation amplifier with automatic differential-pair matching", Solid-State Circuits (ISSCC), IEEE International Conference, Feb. 17-21, 2013, San Francisco, CA, USA, pp. 178-179, DOI: 10.1109/ISSCC.2013.6487689.
Borghi et al., "A power-efficient analog integrated circuit for amplification and detection of neural signals", Engineering in Medicine and Biology Society (EMBC), Annual International Conference of the IEEE, Aug. 20-25, 2008, Vancouver, BC, Canada, pp. 4911-4915, DOI: 10.1109/IEMBS.2008.4650315.
Burt et al., "A Micropower Chopper-Stabilized Operational Amplifier Using a SC Notch Filter With Synchronous Integration Inside the Continuous-Time Signal Path", IEEE Journal of Solid-State Circuits, Dec. 2006, First Published: Nov. 20, 2006, vol. 41, No. 12, pp. 2729-2736, DOI: 10.1109/JSSC.2006.884195.
Chandrakumar et al., "A 2µW 40mVpp linear-input-range chopper-stabilized bio-signal amplifier with boosted input impedance of 300MΩ and electrode-offset filtering", Solid-State Circuits (ISSCC), IEEE International Conference, Jan. 31 to Feb. 4, 2016, San Francisco, CA, USA, pp. 96-97, DOI: 10.1109/ISSCC.2016.7417924.
Chandrakumar et al., "A High Dynamic-Range Neural Recording Chopper Amplifier for Simultaneous Neural Recording and Stimulation", IEEE Journal of Solid-State Circuits, vol. 52, No. 3, Mar. 2017, First Published: Jan. 27, 2017, pp. 645-656, DOI: 10.1109/JSSC.2016.2645611.
Enz et al., "Circuit techniques for reducing the effects of op-amp imperfections: autozeroing, correlated double sampling, and chopper stabilization", Proceedings of the IEEE, Nov. 1996, vol. 84, No. 11, pp. 1584-1614, DOI: 10.1109/5.542410.
Fan et al., "A 1.8 µW 32 nV/√Hz Capacitively-Coupled Chopper Instrumentation Amplifier in 65 nm CMOS for Wireless Sensor Nodes", IEEE JSSC, Jul. 2011, vol. 46, No. 7, pp. 1534-1543.
Kusuda, "Auto Correction Feedback for Ripple Suppression in a Chopper Amplifier", IEEE Journal of Solid-State Circuits, Aug. 2010, First Published: Jul. 23, 2010, vol. 45, No. 8, pp. 1436-1445, DOI: 10.1109/JSSC.2010.2048142.
Muller et al., "A 0.013 mm2, 5 µw, DC-Coupled Neural Signal Acquisition IC with 0.5 V Supply", IEEE JSSC, Jan. 2012, vol. 47, No. 1, pp. 232-243.
Muller et al., "A miniaturized 64-channel 225µW wireless electrocorticographic neural sensor", IEEE ISSCC, Feb. 2014, pp. 412-413.
Wattanapanitch et al., "An Energy-Efficient Micropower Neural Recording Amplifier", IEEE Transactions on Biomedical Circuits and Systems, vol. 1, No. 2, Jun. 2007, pp. 136-147.
Wu et al., "A Chopper Current-Feedback Instrumentation Amplifier With a 1 mHz 1/f Noise Corner and an AC-Coupled Ripple Reduction Loop", IEEE Journal of Solid-State Circuits, Dec. 15, 2009, vol. 44, No. 12, pp. 3232-3243, DOI: 10.1109/JSSC.2009.2032710.
Xu et al., "A160 µW8-Channel Active Electrode System for EEG Monitoring", IEEE Transactions on Biomedical Circuits and Systems, Dec. 2011, First Published: Nov. 11, 2011, vol. 5, No. 6, pp. 555-567, DOI: 10.1109/TBCAS.2011.2170985.

* cited by examiner

HIGH DYNAMIC RANGE SENSING FRONT-END FOR NEURAL SIGNAL RECORDING SYSTEMS

CROSS-REFERENCE TO RELATED APPLICATIONS

The present application claims priority under 35 U.S.C. § 119(e) to U.S. Provisional Application No. 62/058,017, entitled "Simple, Area-Efficient Ripple-Rejection Technique for Chopped Bio-Signal Amplifiers," filed on Sep. 30, 2014, the disclosure of which is incorporated by reference herein in its entirety.

STATEMENT OF FEDERALLY SPONSORED RESEARCH

This invention was made with Government support under Grant No. 084708 awarded by the National Science Foundation. The Government has certain rights in this invention.

FIELD OF THE INVENTION

The present invention generally relates to bio-signal amplifiers and more specifically to high dynamic range front-ends for neural signal recording systems.

BACKGROUND

There has been great interest in the neuroscience community in decoding the functioning of the brain. Among the various methods used, analysis of the recordings of the electrical activity of neurons has been among the most important tools available. These recordings can be indispensable for understanding and diagnosing neurological disorders like epileptic seizures, in the creation of brain-machine interfaces, and for neuro-prosthetic technologies to aid paralyzed patients. Further, modern neuroscience is attempting to "close the loop" with the brain, by stimulating specific areas using current pulses, and recording neuronal responses to learn and adapt the stimulation patterns. For example, it has been demonstrated in a limited number of patients that stimulating certain regions of the entorhinal cortex of the brain could improve memory function.

Typically, extracellular recordings of neural signals occupy a frequency band from 1 Hz to about 5 kHz, and have relatively small amplitudes, ranging from 1 $mV_p$ for Local Field Potentials (LFPs) to 100 $\mu V_p$ for Action Potentials (APs). Due to their small amplitudes, neural signals are often amplified before digitization. Where the peak input-signal amplitudes are on the order of 1 mV, the input-referred noise of an amplifier should be less than 4 $\mu V_{rms}$ for 8-bit resolution. Thus, low-noise bio-signal amplifiers could be utilized in various signal recording systems including (but not limited to) recording neural signals.

SUMMARY OF THE INVENTION

Turning now to the drawings, a high dynamic range sensing front-end for bio-signal recording systems in accordance with embodiments of the invention are disclosed. In one embodiment, a bio-signal amplifier includes an input signal comprising an input voltage and an input current, where the input signal is modulated to a predetermined chopping frequency; a first amplifier stage that includes a first input configured to receive the modulated input signal and generate a first output, where the first output comprises an offset current and a portion of the modulated input current; a parallel-RC circuit connected to the first amplifier stage and configured to receive the first output and generate a parallel-RC circuit output by selectively blocking the offset current utilizing at least one RC resistor and at least one RC capacitor; a second amplifier stage connected to the parallel-RC circuit that includes a second input configured to receive the parallel-RC circuit output and generate a second output, where the second output is an amplified version of the input signal with ripple-rejection.

In a further embodiment, the bio-signal amplifier also includes an auxiliary path configured for boosting input impedance by pre-charging at least one input capacitor.

In another embodiment, the second output and the first input of the bio-signal amplifier are connected by a DC-servo feedback loop that includes an integrator that utilizes a duty-cycled resistor, where the duty-cycled resistor is connected in series to a DC-servo feedback switch configured to periodically remove the duty-cycled resistor from the DC-servo feedback loop.

DETAILED DESCRIPTION OF THE DRAWINGS

Turning now to the drawings, a high dynamic range sensing front-end for bio-signal recording systems in accordance with embodiments of the invention are illustrated. In many embodiments, the front-end can be implemented as a complete Capacitive-coupled Chopper-Stabilized Instrumentation Amplifier (CCIA) that incorporates a variety of techniques as further discussed below. In several embodiments, the CCIA can include an auxiliary path configured to pre-charge capacitors for boosting input impedance as further described below. In various embodiments, the CCIA can also incorporate a 2-stage chopper-stabilized amplifier (CSA) that utilizes a parallel-RC impedance circuit for ripple rejection (RR). As further described below, such CSA with RR can include a first amplifier stage configured to receive an input signal that is modulated to a chopping frequency and connected to a parallel-RC impedance circuit where an output ripple is attenuated by selectively blocking an offset current flowing from the first amplifier stage to a second amplifier stage. In addition, the CCIA can also include a DC-Servo feedback loop configured to high-pass filter for electrode offset rejection utilizing a duty-cycled resistor as described further below. In a variety of embodiments, the CCIA can also include an anti-alias filter prior to generating an output signal.

Although discussed in the context of bio-signals and/or neuro signals and their respective amplifiers, the proposed systems and methods can be utilized with a variety of signals requiring amplification and thus are not limited to bio-signals, neuro signals or any particular recording system. Systems and methods for implementing a high dynamic range sensing front-end in accordance with embodiments of the invention are further discussed below.

Conventional Bio-Signal Front-Ends

A neural signal recording system typically calls for a system that is small, fully implantable, consumes very low power while processing several channels, and can wirelessly transmit data to terminals such as (but not limited to) servers and/or host computers. In addition, neuroscientists also seek the capability to record neural data while simultaneously stimulating neurons. To ensure patient safety and compliance with FDA regulations, such systems face a unique set of design challenges.

Figure 1A:
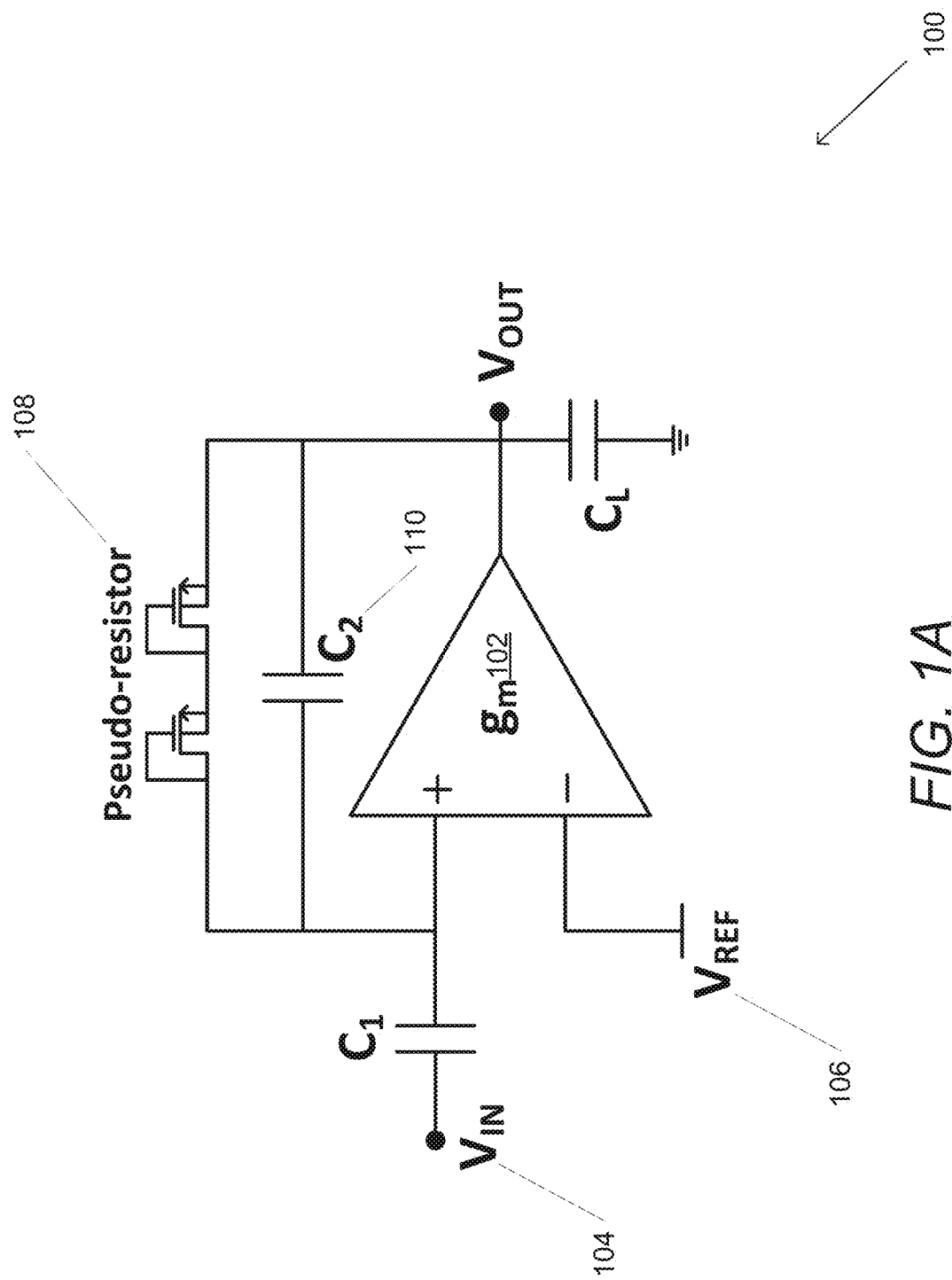
FIG. 1A is a schematic diagram illustrating an amplifier with an AC-coupled input, capacitive feedback and a pseudo-resistor in accordance with the prior art.

Although significant progress has been made, conventional biomedical recording front-ends fall short of meeting the current design challenges. One of the most popular topologies for bio-signal recording front-ends is the capacitive feedback amplifier that utilizes pseudo-resistors. A schematic diagram illustrating an AC-coupled feedback amplifier using pseudo-resistors in accordance with the prior art is illustrated in FIG. 1A. The amplifier 100 can have an associated gain $g_m$ 102, where the amplifier can be configured to receive an input voltage signal 104 relative to a reference voltage 106. Typically, the feedback loop can include a MOS-BJT pseudo resistor 108 for implementing a high-pass corner for electrode offset rejection, where the MOS-BJT resistor can provide a TΩ of resistance. The use of such pseudo resistors can reduce the size and the area consumed by the accompanying feedback capacitor 110. Such topologies focus on reducing the input-referred noise power and improving the noise-efficiency factor (NEF) since the power consumed by the front-end is often dictated by the input-referred noise constraint. To get the lowest thermal noise floor for a given bias current, the input pair is often biased in weak inversion, where the $g_m/I_d$ of the device is maximized. The noise contribution of successive amplifier stages is reduced by the gain of the preceding stages, making their noise contribution negligible. This is also the reason why most recording systems incorporate a high (approx. 40 dB) gain in the first stage. Further, the NEF of such front-end amplifiers can be improved by using an inverter-based amplifier. With careful noise optimization, documented action potential (AP) recording front-ends have achieved an NEF of 2.7 with 7.6 µW power consumption.

Figure 1B:
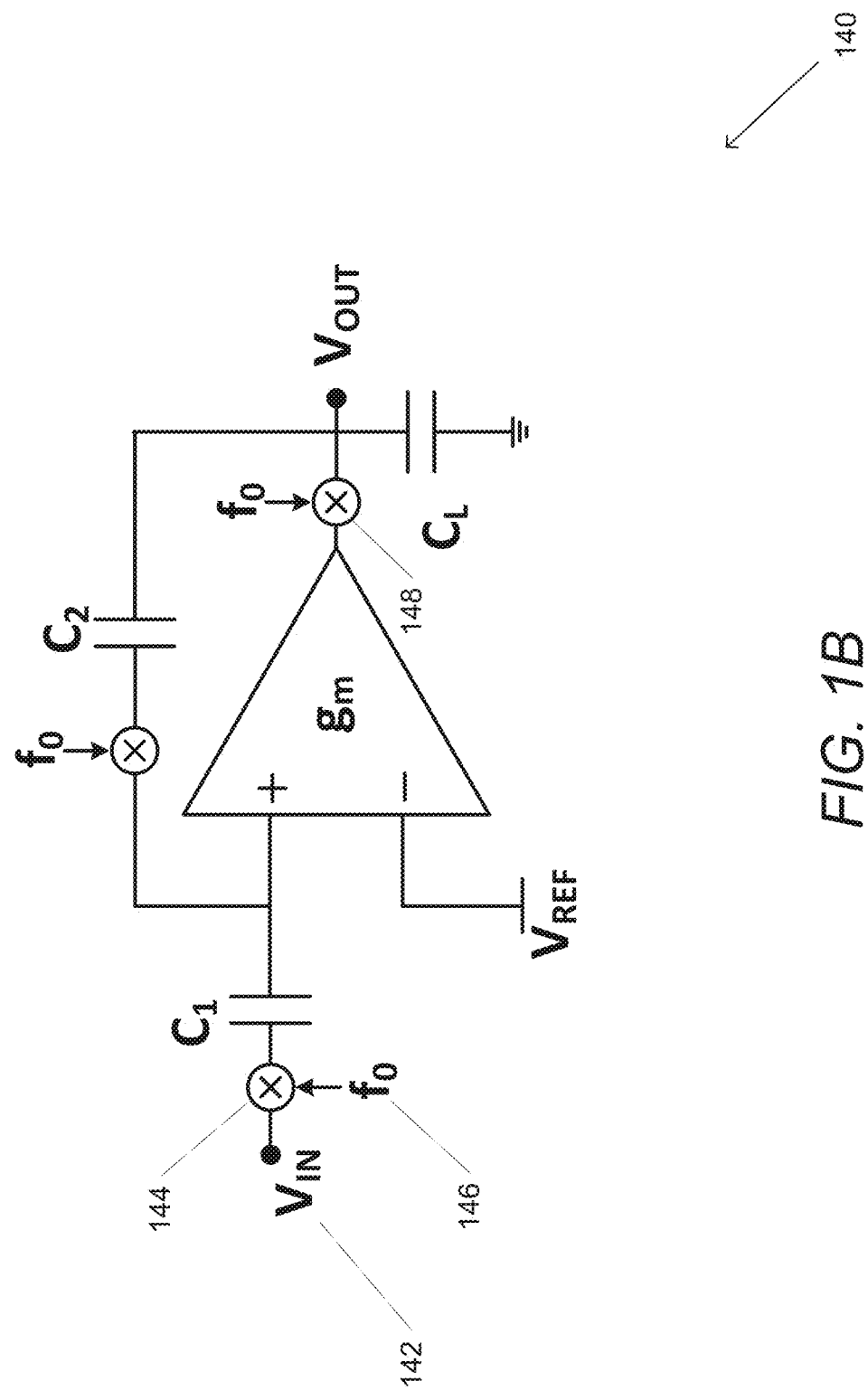
FIG. 1B is a schematic diagram illustrating a conventional chopper-stabilized amplifier (CSA) in accordance with the prior art.

Another popular topology for bio-signal recording front-ends is the chopper-stabilized amplifier (CSA), which allows for reduction in the flicker-noise contribution without the associated brute-force increase in the input device area. A CSA in accordance with the prior art is shown in FIG. 1B. The CSA 140 can be configured to take a signal of interest 142 and up-convert it using a mixer 144 to a chopping clock frequency 146. This process allows the signal to be separated from the low-frequency noise in the frequency domain. A subsequent down conversion using a mixer 148 can translate the signal of interest back to baseband, while the low-frequency noise can be translated to the chopping frequency and filtered. An added benefit of chopping is the high common mode rejection ration (CMRR) achieved in the presence of mismatched input capacitors. Prior work that used this technique has demonstrated an EEG recording front-end that has an NEF of 3.3 with power consumption of 1.8 µW, while providing a CMRR of 130 dB.

Figure 1C:
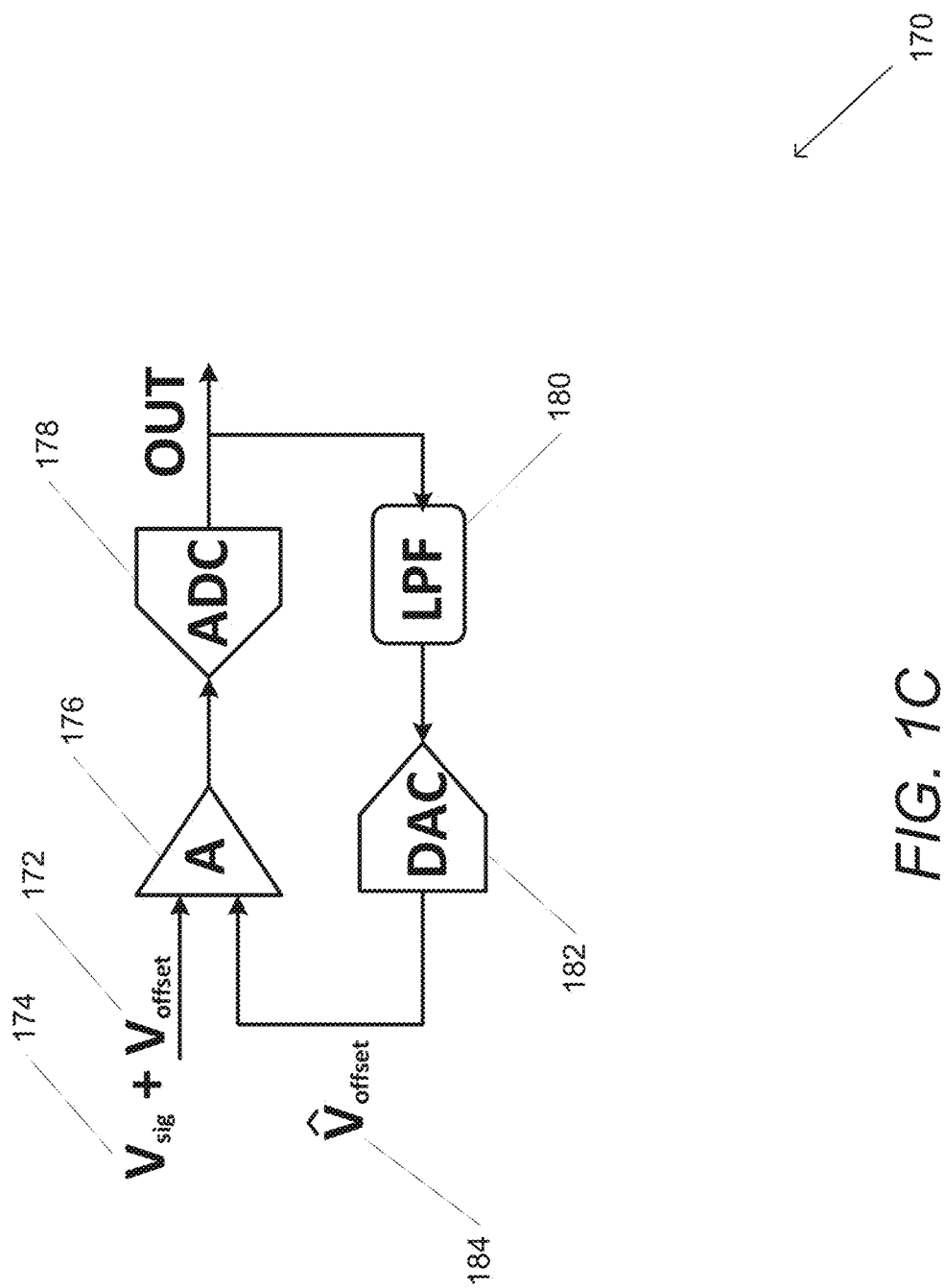
FIG. 1C is a schematic diagram illustrating a DC-coupled mixed-signal servo loop in accordance with the prior art.

Another proposed design is the use of a mixed-signal feedback. A DC-coupled mixed-signal servo loop in accordance with the prior art is shown in FIG. 1C. The low time-constants typically required for AC coupling an input often call for large capacitors, which can dominate the area of an analog front-end. To reduce area, the input can be DC coupled and a DC servo loop can be used to cancel the large DC offsets. As illustrated, the servo loop 170 includes adding a DC offset 172 to the signal of interest 174. The DC coupled signal is then amplified by an amplifier 176 where the analog output is digitized by an analog-to-digital converter (ADC) 178. In the feedback loop, the digitalized output can be filtered using a LPF 180 and converted by to an analog signal 184 using a digital-to-analog converter (DAC) 182. The servo loop can be implemented as a mixed-signal loop since the large time constants for the feedback path of the loop are easy to synthesize in the digital domain. Using this approach, a front-end with an area of 0.013 mm$^2$ has been demonstrated, representing a 10×-reduction over other comparable systems. Such a neural recording front-end can consume 5.04 µW with an NEF of 6. Alternate switched-capacitor implementations of the servo-loop filter that significantly reduce silicon area have also been proposed.

TABLE I

REVIEW OF CONVENTIONAL BIOMEDICAL FRONT-ENDS

| Parameter | [1] | [2] | [3] | [4] | Desired |
|---|---|---|---|---|---|
| Power (μW) | 80 | 7.6 | 1.8 | 5.04 | <3 |
| BW (Hz) | 7.2k | 5.32k | 180 | 10k | 1-5k |
| Noise (μ$V_{rms}$) | 2.2 | 3.06 | 0.95 | 4.9 | 4-5 |
| D.R. (dB) | 60 | 54 | 64 | 35 | 85 |
| THD (%) | 1 | 1 | 0.1 | 2 | 0.005-0.01 |
| Input swing (m$V_p$) | 8.35 | 3.65 | 5 | 0.28 | 50-100 |
| DC $Z_{in}$ (Ω) | ∞ | ∞ | 8M | ∞ | >100M |

Table I summarizes some performance measures of few a conventional bio-signal recording front-ends. While some prior designs allow a system to achieve a low input-referred noise with low power consumption, most of these systems do not address the need for high dynamic-range (D.R.) for bio-signal recording. Typically, the dynamic range of past designs is often limited to 60 dB and the input swing is limited to less than 20 mV. Often, conventional bio-signal recording front-ends incorporate a high voltage-to-voltage gain (40 to 80 dB), which enables the front-end to provide a low input-referred noise without paying a hefty price in power consumption. However, due to the high gain in the system, the large interferers accompanying the signal of interest can easily saturate the front-end. To make matters worse, once the signal chain saturates it can remain saturated for a long period of time due to the large time constants for bringing the circuit back to regular operation.

Figure 2A:
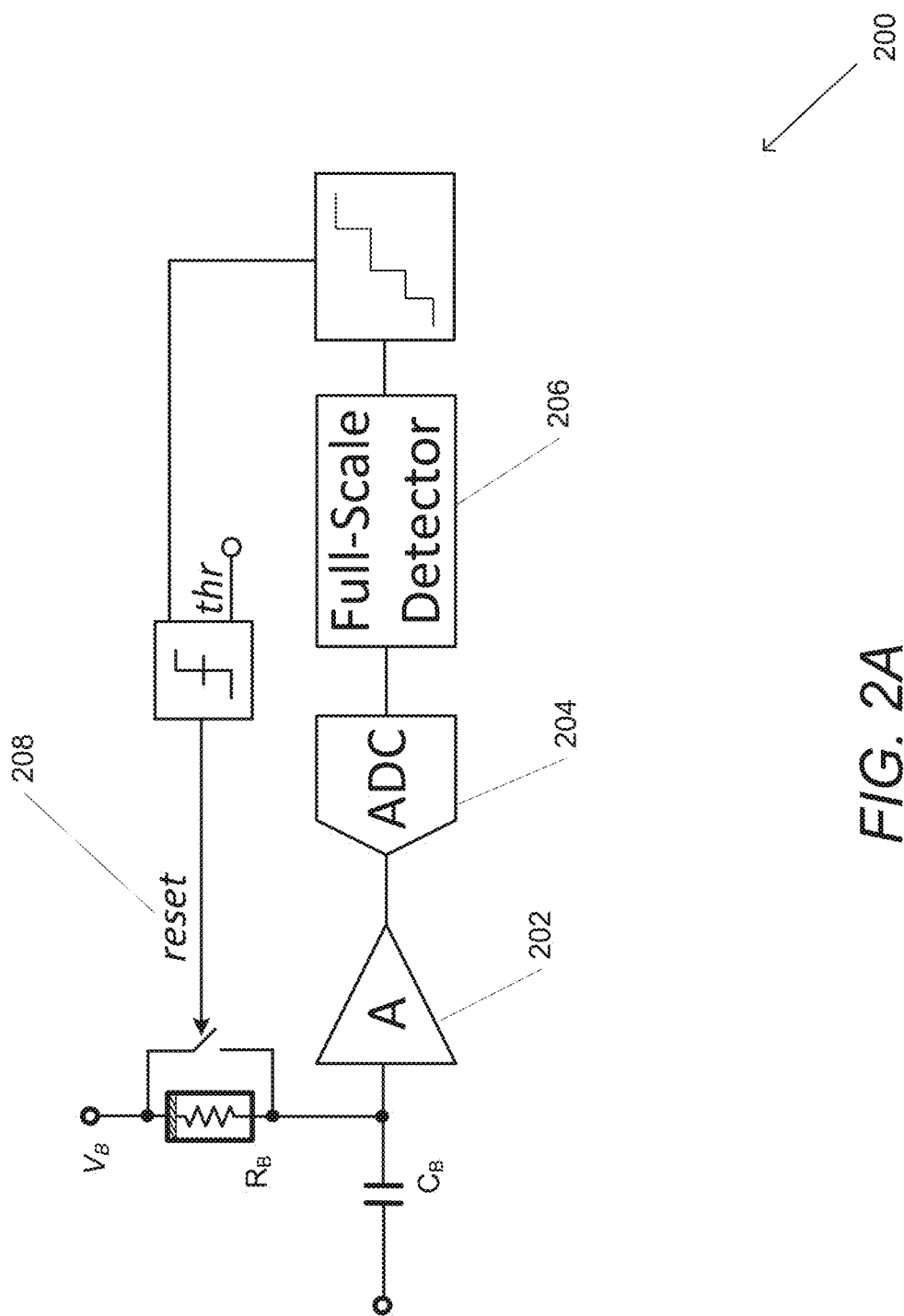
FIG. 2A is a schematic diagram illustrating a system that utilizes a saturation detector in accordance with the prior art.

Proposed solutions to mitigate the problem of signal saturation include using overload recovery schemes, non-linear feedback elements, and mixed-mode feedback loops. A topology that utilizes a saturation detector in accordance with the prior art is shown in FIG. 2A. The system 200 is configured to amplify a signal using an amplifier 202 where the analog output is converted to digital form using an ADC 204. Once saturation is detected using a saturation detector 206, a reset signal 208 is asserted to discharge the high time-constant nodes in the front-end, allowing the circuit to recover quickly from saturation. While this solution significantly speeds up the recovery from saturation, it does not prevent the signal chain from saturating under the continued presence of interferers. Also, all signal data is lost during the duration of the reset operation.

Figure 2B:
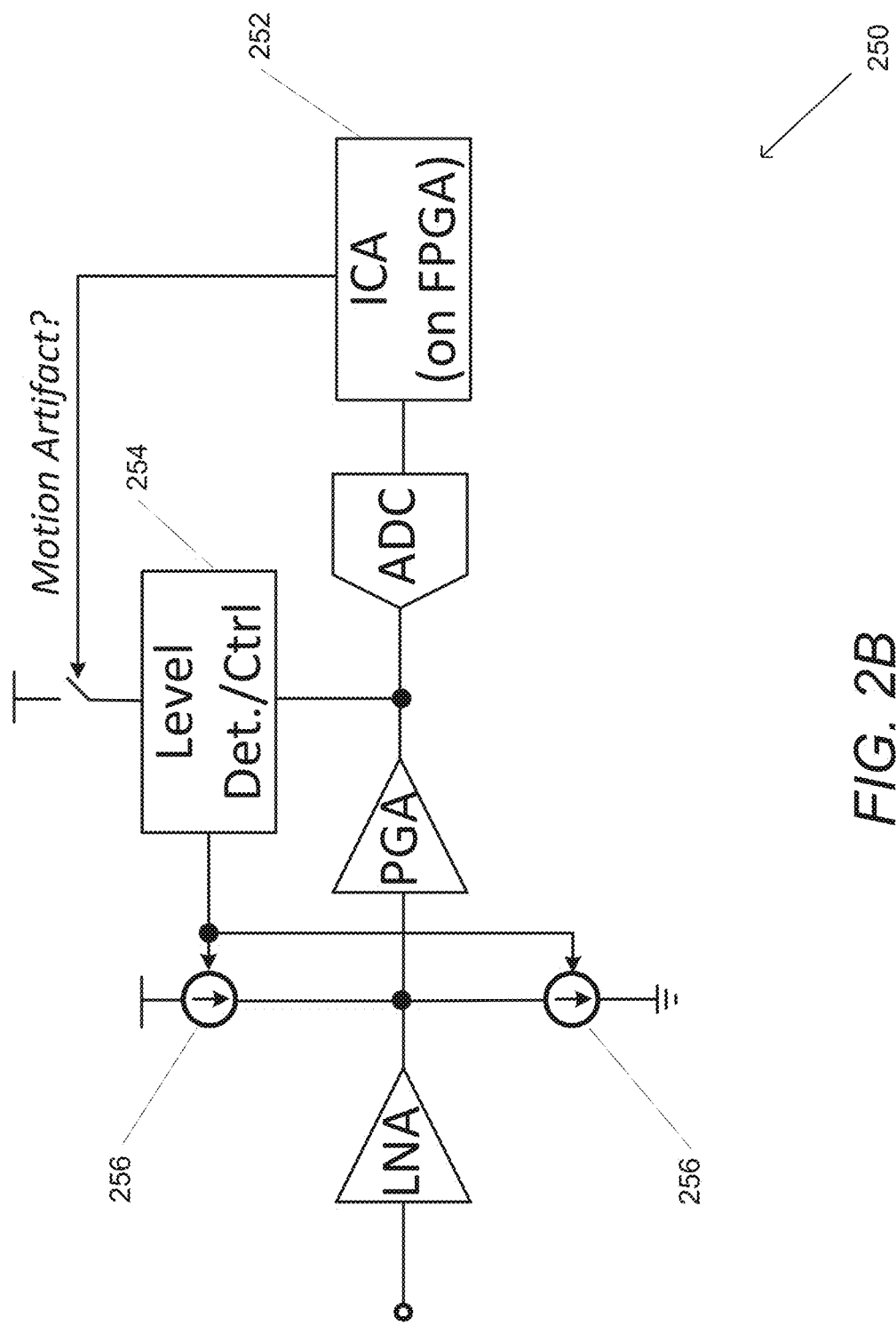
FIG. 2B is a schematic diagram illustrating a system that utilizes an independent-component analysis based process in accordance with the prior art.

Another desired feature of a front-end includes simultaneous stimulation and recording, where the recording system should be able to record neural signals in the presence of large artifacts. An independent-component analysis (ICA) based process to detect the presence of motion artifacts in the recorded data in accordance with the prior art is shown in FIG. 2B. As illustrated in 250, upon detection of motion artifacts by an ICA 252, a combination of a level-detect circuit 254 and DC-level shifters 256 can be used to regulate the DC level at the output of the first stage to move the circuit away from saturation. This design demonstrates a saturation-tolerant input range of 4.4 mV for interferers like motion artifacts, which are slowly varying compared to the signal of interest.

Table I above also reveals that conventional systems can have limited Total Harmonic Distortion (THD) primarily due to the use of nonlinear pseudo-resistors in the feedback network. The pseudo-resistors experience the full output signal swing, which can cause the front-end to have limited linearity. Also, pseudo-resistors can be very sensitive to process and temperature variations (100× resistance variation over process and temperature corners), making them unreliable to realize an accurate corner frequency. Although a CSA can provide a good power-noise trade-off, CSAs typically also have considerable limitations as further discussed below. Finally, some have proposed mixed-signal feedback architectures to achieve low area, but such designs can compromise on signal quality and have limited capacity to handle interferers. Typically, the open-loop nature of the amplifier in the signal band limits the THD to −37 dB for a 0.5 m$V_p$ input signal.

Although specific conventional bio-signal front-ends are discussed above with respect to FIGS. 1-2B and Table I, any of a variety of bio-signal front-ends as appropriate to the requirements of a specific application can be considered in accordance with embodiments of the invention. Limitations of conventional CSAs as front-end amplifiers are discussed further below.

Considerations of Conventional Chopper-Stabilized Amplifiers

A chopper-stabilized amplifier (CSA) can be utilized as a front-end amplifier for neural recording systems. As discussed above with respect to FIG. 1B, a CSA can eliminate the low-frequency flicker noise contribution from the amplifier and can be designed for minimal power with a given input-referred noise requirement. However, the conventional CSA can have significant limitations. One such limitation can be the reduced input impedance due to the action of the input mixer and the input capacitor, resulting in the input of the CSA appearing as a switched-capacitor resistance. Such reduced input impedance can load an associated electrode, which can attenuate the signal of interest as the electrode is typically a poor voltage source. Also, the electrode-tissue interface can generate DC offset voltages on the order of 50 mV, which can generate DC currents if the recording front-end input-impedance is relatively small. Further, these DC currents, if allowed to flow for long periods of time, can corrode the electrode and cause tissue damage at the electrode-tissue interface.

Another drawback of the CSA is their limited linearity and dynamic range. The use of pseudo-resistors to create a low-frequency high-pass filter is a popular technique. However, as discussed above, the nonlinearity of the pseudo-resistors can generate large harmonic tones and distorts the output, thus limiting the maximum input signal swing of existing front-ends to a few mV. This reduced input swing capability can limit the dynamic range of such front-ends to 9-10 bits.

In addition, the input DC offset experienced by a CSA is typically not filtered. Thus when the input signal of the CSA is up-modulated to the mixer clock frequency before being amplified, any input DC signal will be translated to the pass-band of the amplifier, and thus experience the full mid-band gain of the CSA. Unlike the conventional capacitively-coupled amplifier, there is no inherent high-pass filtering possible by introducing a simple resistor in the feedback network. As the DC offset can be 50× larger than the accompanying neural signals, this offset can saturate the amplifier if it is not filtered out.

Finally, convention CSAs suffer from the generation of an output ripple. As discussed above, the offset and flicker noise of the CSA are up-modulated before they appear at the output. This up-modulated signal can potentially create large ripples at the amplifier output, significantly reducing the available linear range. The reduced output swing can directly impact the dynamic range of the recording front-end. Processes for boosting input impedance by pre-charging using an auxiliary path in accordance with embodiments of the invention as discussed further below.

Auxiliary Path Pre-Charge for Boosting Input Impedance

Figure 3:
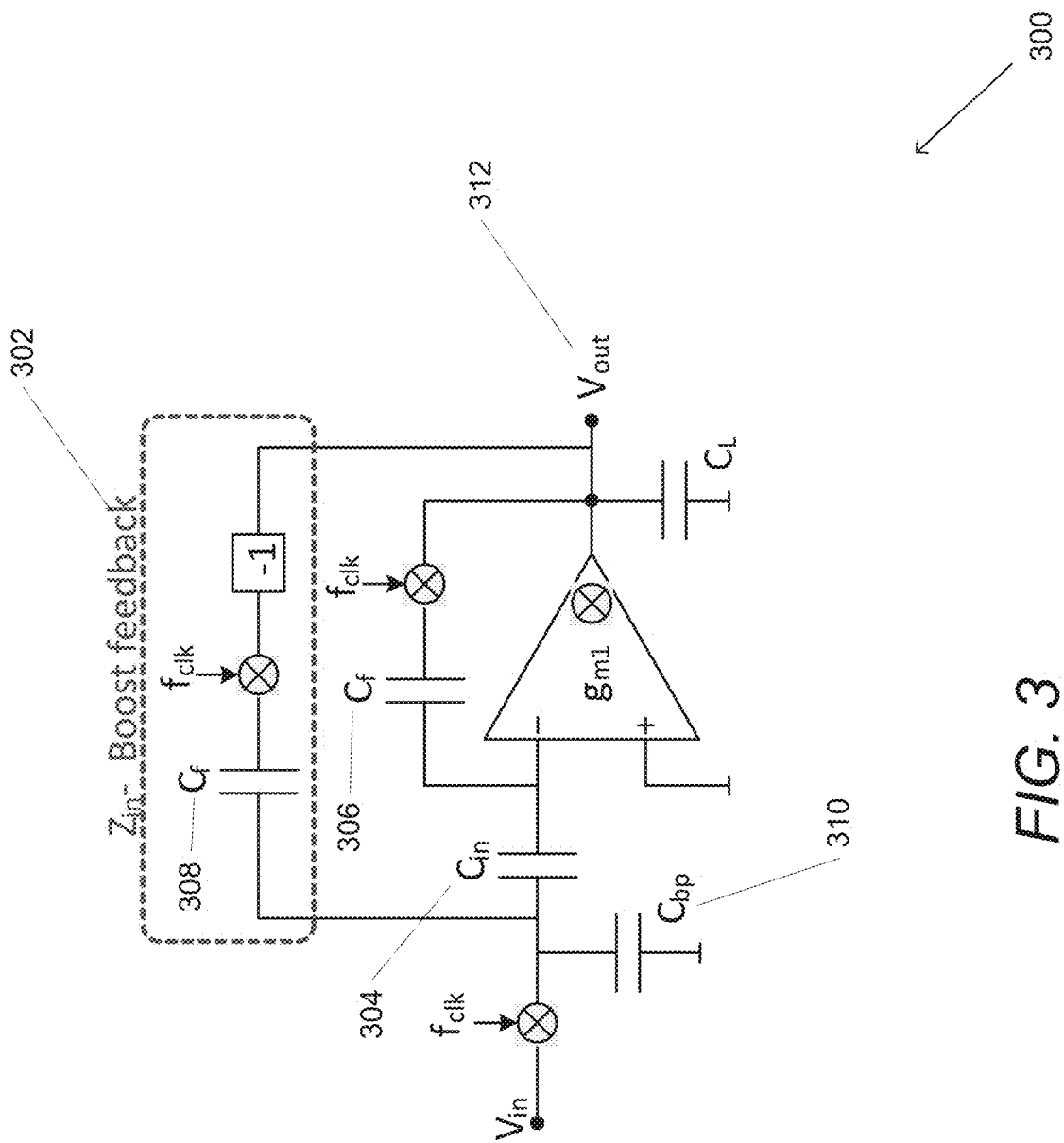
FIG. 3 is a schematic diagram illustrating a CSA that utilizes a positive-feedback loop to boost input impedance in accordance with prior art.

As discussed above, the reduced input impedance of a CSA can hinder its application as a neural signal recording front-end. In conventional systems, a positive-feedback loop has been proposed to boost the input impedance. A CSA that utilizes a positive-feedback loop to boost the input impedance in accordance with the prior art is shown in FIG. 3. If the feedback capacitor in the positive-feedback loop is sized to be exactly $C_{in}/(A_o-1)$, then the input impedance would be boosted to infinity. As illustrated in 300, a positive-feedback loop 302 is utilized to increase the input impedance of the CSA. Here, the closed-loop gain $A_o$ is equal to $C_{in}$ 304 divided by $C_f$ 306. Due to limited matching, the positive-feedback capacitor 308 can be made equal to $C_f$ 306 boosting the input impedance by a factor of $A_o$. For typical neural recording amplifiers, $A_o$ can be around 100, which would be a significant boost to the input impedance. But the presence of parasitic capacitors, like the bottom-plate capacitance $C_{bp}$ 310, can limit the input-current cancellation provided by the positive feedback path 302. From past designs, it can be seen that this technique is limited in practice to boost the inputting impedance by a factor of 5-10. The past design realized an input impedance of 30 MΩ, which was boosted from 6 MΩ. Another drawback of the positive-feedback loop is that an electrode offset should be present at the amplifier output. Typically, this is not satisfied if a suitable high-pass filtering technique is implemented, such that any DC component at the output $V_{out}$ 312 is attenuated. Thus, the positive-feedback loop is rendered inoperative when the output DC component is filtered, which will be the case for any practical neural recording system.

Figure 4:
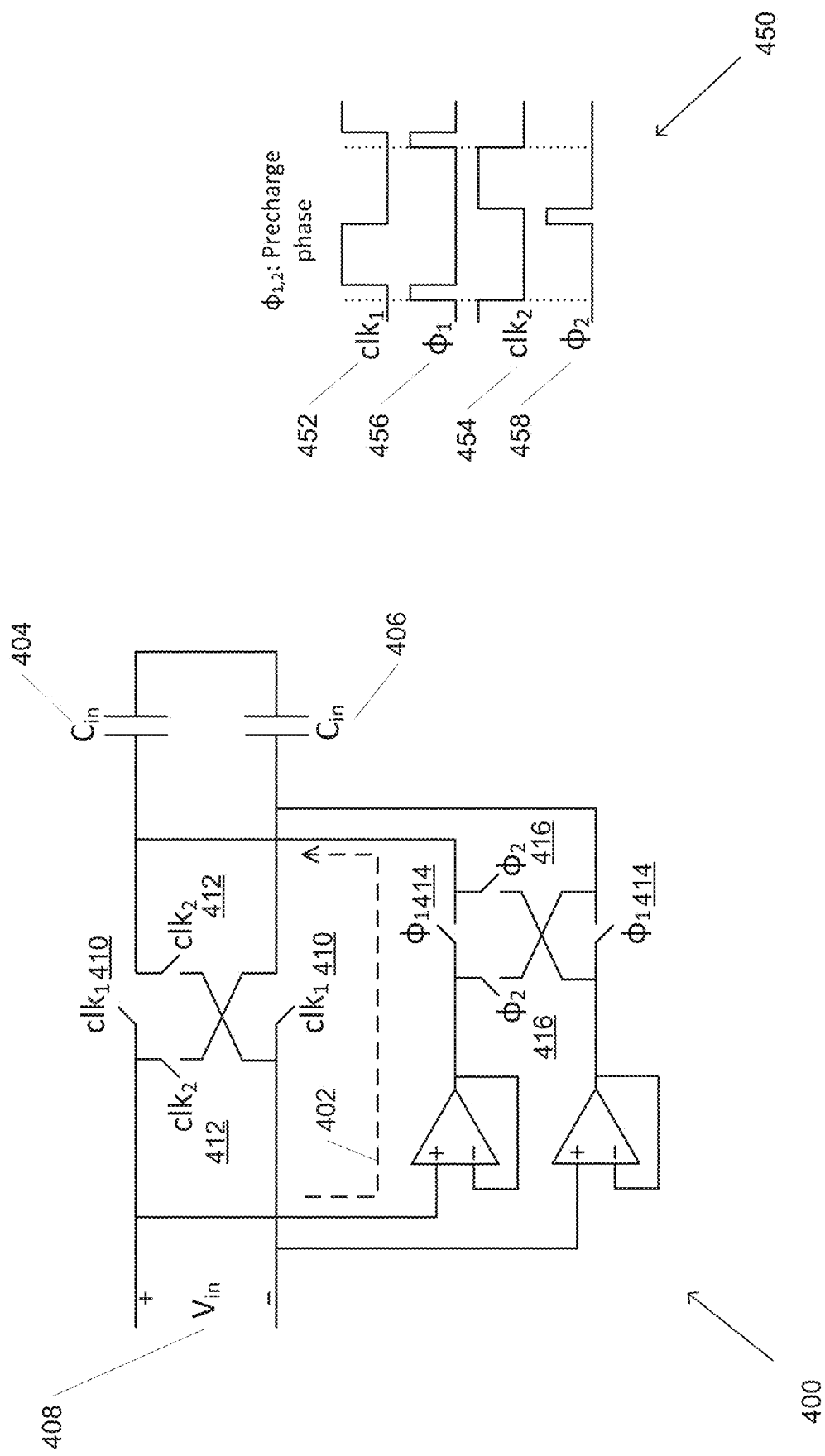
FIG. 4 is a schematic diagram illustrating an auxiliary path for pre-charging input capacitors in accordance with an embodiment of the invention.

A solution to this parasitic-capacitance sensitivity problem could be to use a programmable capacitor bank in the positive feedback loop. For example, assuming a chopping frequency of 25 kHz, the capacitor bank should set the capacitance with an accuracy of a few fF, which can be difficult to implement. In many embodiments of the invention, an auxiliary path can be utilized to pre-charge input capacitors to the correct potential before connecting input electrodes. An auxiliary path for pre-charging input capacitors in accordance with an embodiment of the invention is shown in FIG. 4. In various embodiments, the input capacitor boost technique includes a system 400 that utilizes an auxiliary path 402 for pre-charging input capacitors 404, 406 to a predetermined potential before connecting the input electrodes. The auxiliary path can be set to an enabled configuration to charge the input capacitors or to a disabled configuration for connection to the electrodes (i.e. connection to the input signal 408). The configuration of the auxiliary path can be controlled based upon two sets of switches 410, 412 that are either open or closed as described in the timing diagram illustrated in 450. Typically, clock 1 452 and clock 2 454 are in opposite phases at any given time. Further, in-between changes to a new clock-phase, there can be a pre-charge phase 1 456 and a pre-charge phase 2 458 each corresponding to control of two sets of switches 414, 416 that are either open or closed, respectively, as illustrated in 450.

In many embodiments, before the input mixer changes to a new clock-phase, the auxiliary path 402 is enabled, which charges the input capacitors $C_{in}$ 404, 406 to the input voltage $V_{in}$ 408 through the auxiliary-path buffers. After the input capacitors 404, 406 have been charged, the auxiliary path can be disabled and the electrodes connected to the input capacitors. Thus, all the charge utilized by the input capacitors is provided by the supply voltages, through the buffers in the auxiliary path. The input electrodes would ideally provide zero charge, making the input impedance appear infinite at low frequencies. In practice, due to the finite speed and open-loop gain of the auxiliary path buffers, the input capacitors typically do not charge to exactly $V_{in}$. The residual error during the pre-charge phase 456, 458 can limit the factor by which the input impedance can be boosted. In several embodiments, this error can be easily set below 1% by allowing 3-4 time-constants for the auxiliary path buffers to settle, thus boosting the input impedance by at least 100×. Any parasitic capacitance (like the bottom-plate capacitor illustrated in FIG. 3) will also get pre-charged, thus making this technique insensitive to parasitic capacitance. Also, this technique relies on the offset appearing at the electrode itself, and can thus be used simultaneously with a high-pass filtering technique that filters out the DC component from the amplifier output. This can provide significant advantage over the positive feedback technique as illustrated in FIG. 3.

In various embodiments, the power utilized in the auxiliary path buffers is determined by the settling requirement of the buffers. Considering typical values, the input capacitance $C_{in}$ can be on the order of ~1 pF, and the chopping frequency can be 25 kHz. Assuming that the auxiliary path needs to settle within 1/16th of the time period of a phase of the chopping clock (i.e. within 20 μs/16 for a 25 kHz chopping clock), the settling time available is 1.25 μs. For $4_T$ settling, the bandwidth of the buffer should be ~500 kHz. For a 1 pF load capacitance and a single-stage op-amp, the transconductance is ~3 μA/V. This would call for a bias current of 250 nA per buffer. But the buffer bias current can be duty-cycled, thus making the average bias current requirement to be 500 nA/16=31.25 nA. Thus, the power overhead for the auxiliary path buffers is small, about 2% of the bias current of a complete implementation of a CCIA as further discussed below.

Along with the power utilized, the noise contribution of the auxiliary path buffers should also be considered. At the end of the pre-charge phase 456, 458, the output noise of the auxiliary path buffers gets sampled on to the input capacitors $C_{in}$ 404, 406. This sampled noise voltage can be very large as compared to the required input-referred noise. But during the next phase when $C_{in}$ is connected to the electrodes, the sampled noise voltage gets discharged through the input electrodes. If the discharge time constant is sufficiently small, then the sampled noise is discharged to near zero. As the amplifier output will be sampled at the end of this discharge phase, the noise contribution from the auxiliary path buffers can be kept small.

The auxiliary-path buffer, being directly shorted to the electrodes, should support an Input-Common-Mode Range (ICMR) and Output-Common-Mode Range (OCMR) of $\pm V_{in,offset}$, where $V_{in,offset}$ is the maximum electrode DC offset. Since this offset voltage can be ±50 mV, the ICMR and OCMR of the auxiliary-path buffers should be at least ±50 mV.

Although specific processes for boosting input impedance by pre-charging at least one input capacitor using an auxiliary path are discussed above with respect to FIG. 4, any of a variety of processes and configurations for boosting input impedance using auxiliary paths as appropriate to the requirements of a specific application can be utilized in accordance with embodiments of the invention. An area-efficient ripple-rejection (RR) technique in accordance with embodiments of the invention is discussed further below.

Bio-Signal Amplifiers and Chopping

Bio-signal amplifiers can be can be fabricated utilizing deep-submicron CMOS technologies for ease of integration with digital and Radio-Frequency (RF) circuitry. Typically, the amplifier topology utilizes a differential pair with capacitive feedback, where the input-referred noise of the amplifier is proportional to the input-referred noise of the differential pair. The two main contributors of noise of a differential pair are the thermal noise and the flicker noise of the input transistors. In many embodiments, a flicker noise corner frequency can be defined as the frequency where thermal and flicker noises equally contribute to the noise Power Spectral Density (PSD). Since neural signals of interest typically start from 1 Hz, the flicker noise corner frequency should ideally be less than 1 Hz for minimal contribution of flicker noise to the overall amplifier noise.

For a thermal noise floor of 53.4 nV/√Hz, and for input-device sizes of 100 μm in width by 1 μm in length, the simulated flicker noise corner frequency of a PMOS differential pair can be approximately 460 Hz when using a 65 nm CMOS process. This implies that the area of the input devices should be increased by a factor of 460 to achieve a 1 Hz flicker noise corner frequency. However, a large device area can significantly increase the input capacitance of an amplifier, which in turn can degrade the closed-loop input-referred noise of the amplifier. In various simulations, even with compromises between increasing input capacitance of the amplifier and reducing the flicker noise corner, the flicker noise corner has been measured higher than 800 Hz. Such a high flicker noise corner may be unacceptable in many applications including in measuring neural signals since many neural signals of interest lie between 1 Hz and 100 Hz. Conventionally, chopping can be utilized to achieve flicker noise corner frequency in the range of 1 Hz. However, chopping produces a large ripple where an up-modulated flicker noise and offset show up as ripples at the output of the amplifier.

Figure 5:
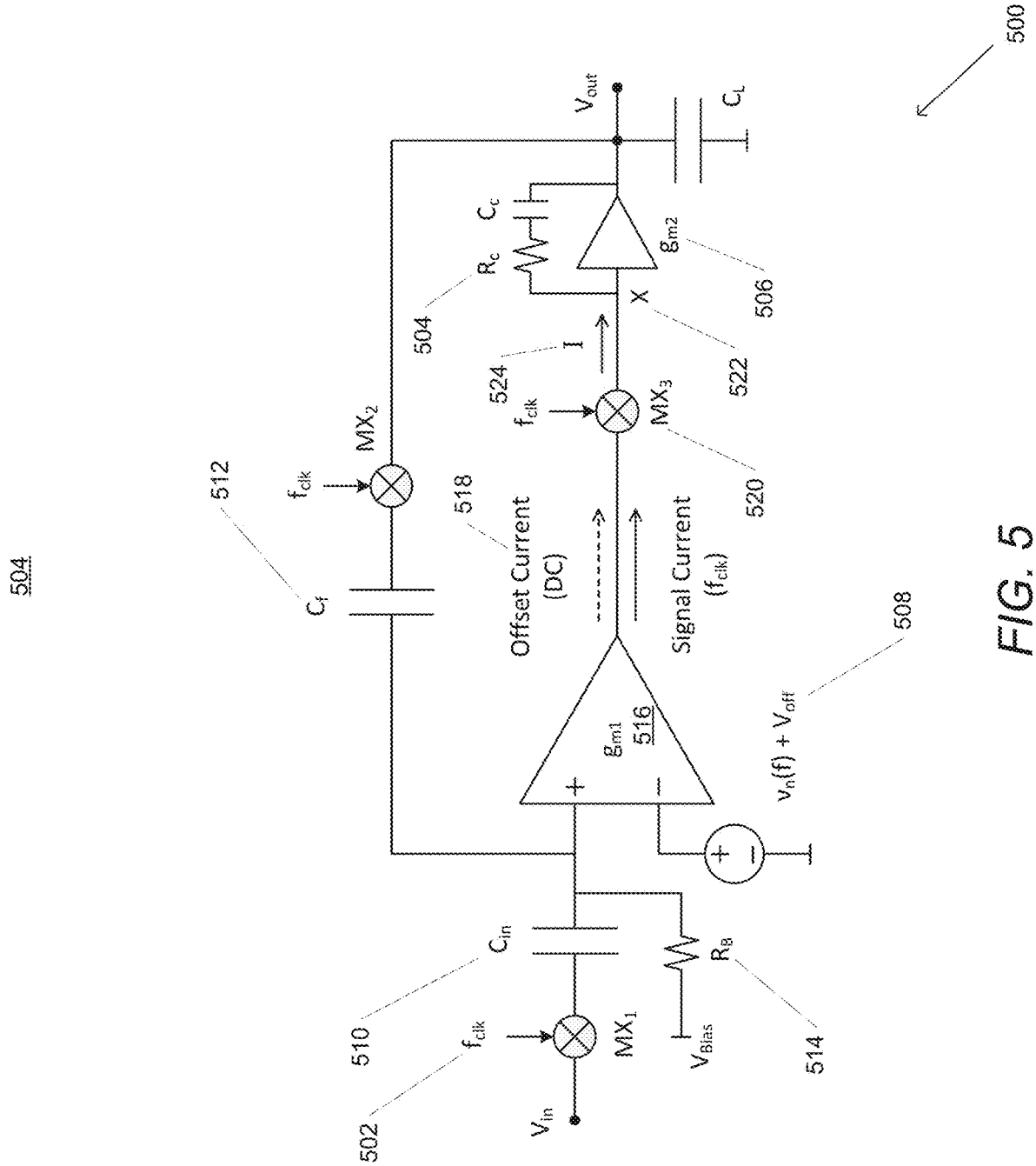
FIG. 5 is a schematic diagram illustrating a conventional 2-stage CSA in accordance with the prior art.

A conventional 2-stage amplifier using chopper-stabilization in accordance with the prior art is illustrated in FIG. 5. As illustrated, the 2-stage CSA 500 can include a chopping frequency denoted by $f_{clk}$ 502. To reduce the effect of the right-half-plane zero on phase margin, Rc 504 can be chosen to be equal to $1/g_{m2}$, where $g_{m2}$ 506 is the gain associated with the second stage amplifier. The loop-gain for the DC offset $V_{off}$ 508 is typically low, because of the high-pass filter formed by the feedback network including the elements $C_{in}$ 510, $C_f$ 512 and the bias resistor RB 514. Hence, there is no feedback present for the amplifier DC offset, and the gain associated with the first stage amplifier $g_{m1}$ 516 acts as an open-loop transconductance. The output current 518 from the first stage due to the DC offset is $g_{m1}V_{off}$. This current is chopped by the mixer $MX_3$ 520 and flows into node X 522. The transfer function $V_{out}/I$ (where I is the chopped current) for $\omega \sim \omega_{clk}$ is given by $$V_{out}(s) = -\frac{I(s)}{sC_C}\left(\frac{1}{1+(s/\omega_{p2})}\right) \quad (1)$$

where $\omega_{p2}$ is the non-dominant pole frequency given by $g_{m2}/C_L$. For stability, $\omega_{p2}$ is a factor of 3-5 higher than the closed-loop bandwidth. And it is typical to choose $f_{clk}$ that is a factor of 5-10 higher than the closed-loop bandwidth. Thus, $V_{out}/I$ is not an ideal integrator.

The output ripple can be approximated by considering only the fundamental component of the chopping current I 524, as shown below $$V_{ripple,PP} \approx 2V_{off}\left[\frac{(4/\pi)\omega_o A_o}{\omega_{clk}} \cdot \frac{1}{(1+\omega_{clk}^2/\omega_{p2}^2)^{1/2}}\right] \quad (2)$$

where $A_o$ is the closed-loop gain given by $C_{in}/C_f$, and $\omega_o$ is the closed-loop bandwidth. The ripple estimate given by equation (2) is typically more accurate than the estimates which assume that the $2^{nd}$ amplifier stage has infinite bandwidth (i.e. $\omega_{p2} \approx \infty$). From equation (2), for an input offset of 5 mV, a closed-loop gain of 100, and $\omega_{clk} = \omega_{p2} = 5 \omega_o$, the output ripple amplitude is 180 m$V_{pp}$. Given that the output signal of interest is about 100 mV, such a large ripple is unacceptable and should be attenuated before digitization.

Although specific examples of conventional 2-stage CSAs and their characteristics are discussed above with respect FIG. 5, any of a variety of conventional 2-stage CSAs as appropriate to the requirements of a specific application can be utilized in accordance with embodiments of the invention. Bio-signal amplifiers utilizing RR techniques in accordance with embodiments of the invention are further discussed below.

Bio-Signal Amplifiers with Ripple-Rejection

Figure 6:
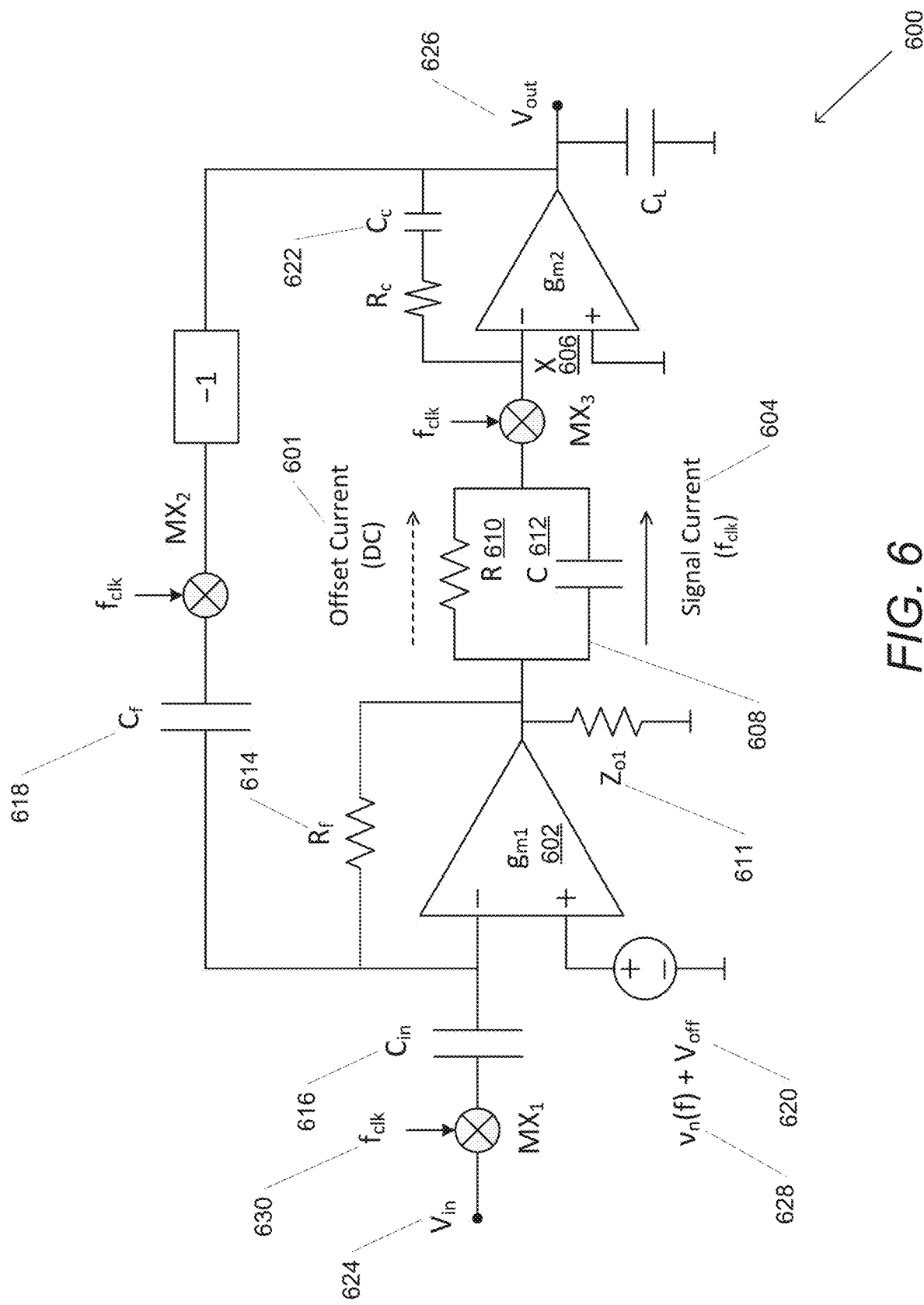
FIG. 6 is a 2-stage CSA with ripple-rejection (RR) in accordance with an embodiment of the invention.

The output ripple can be minimized by employing various feedback techniques. For example, a ripple-rejection feedback loop can be used where the output ripple is down-converted and utilized as an input to an integrator. The output of the integrator is then summed with the output current of $g_{m1}$, thus creating a negative feedback loop which nulls the output ripple. In another example, a foreground calibration can be performed to generate a compensating current using a DAC to cancel the offset, where the compensating current is then fed to the output of $g_{m1}$. Typically, the input devices of $g_{m1}$ can be implemented using multiple small devices that can be redistributed between the positive and negative signal paths to reduce the offset. In a further example, a switched-capacitor notch filter can be introduced between the de-modulation mixer $MX_3$ and the virtual-ground of $g_{m2}$. The notch-filter attenuates signals at the chopping frequency, thus preventing the chopped offset currents from flowing into $g_{m2}$. However, the notch filter can add unwanted phase delay to the signals of interest, which complicates the compensation of the amplifier feedback loop. Although the various feedback techniques can minimize output ripples, they also introduce large capacitors, or switched-capacitor filters in the signal path that can complicate the compensation of the amplifier. A chopper-stabilized capacitive feedback amplifier, modified for RR, in accordance with an embodiment of the invention is illustrated in FIG. 6. In many embodiments, the primary cause of chopper ripple is the offset current 601 generated by $g_{m1}$ 602. Note that the current produced by the input signal 604 is also flowing from $g_{m1}$ 602 into the second amplifier stage X 606, but this current has power around the chopping frequency. If the offset current 601 is selectively blocked from flowing into the second amplifier stage 606, then the output ripple can be reduced.

In various embodiments, to reduce the offset current 601, a parallel-RC impedance 608 can be added immediately after $g_{m1}$ 602. This impedance can act as an open-circuit to $g_{m1}$ at low-frequencies if R 610 is larger than $Z_{o1}$ 611 (the output impedance of $g_{m1}$). At the chopper frequency, the parallel-RC impedance 608 acts like a short circuit if the impedance of the capacitor C 612 (at $f_{clk}$) is smaller than $Z_{o1}$ 611. In several embodiments, to reduce the gain seen by the offset and flicker noise from $g_{m1}$, a large resistor $R_f$ 614 can be placed in feedback across $g_{m1}$. For signals around DC flowing in the first stage, $g_{m1}$ appears as a unity-feedback voltage buffer, as the feedback from the capacitor divider formed by $C_{in}$ 616 and $C_f$ 618 is broken for DC signals. Thus the offset voltage at the output of $g_{m1}$ 602 is $V_{off}$ 620. This offset voltage can produce a current through the resistor R 610, and this current gets chopped and integrated onto $C_c$ 622 to produce the output ripple. In various embodiments, the amplitude of the ripple is given by $$V_{ripple,PP} \approx \frac{2V_{off}}{g_{m1}R}\left[\frac{(4/\pi)\omega_o A_o}{\omega_{clk}} \cdot \frac{1}{(1+\omega_{clk}^2/\omega_{p2}^2)^{1/2}}\right] \quad (3)$$

From equations (2) and (3), the attenuation of the output ripple arising from the DC offset is given by $g_{m1}R$. In a variety of embodiments, the resistance R 610 can be implemented by a leaky switch that is off, with R≈1 GΩ. With $g_{m1}$≈10 μA/V (typical for bio-signal amplifiers), the output ripple can be attenuated by 80 dB. In many embodiments, the bio-signal amplifier utilizes passive resistors and a small capacitance of 2 pF resulting in an output ripple attenuated by 88 dB.

Apart from suppressing the DC offset of $g_{m1}$, ripple-rejection techniques in accordance with embodiments of the invention can also suppress the flicker noise of $g_{m1}$. The transfer function from $v_n$ (around baseband frequencies) to $V_{out}$ (around $f_{clk}$) for $\omega \ll \omega_{clk}$ is given by $$\frac{V_{out}(s+j\omega_{clk})}{v_n(s)} \approx \frac{8}{\pi^2} \cdot \frac{(1+s(C_{in}+C_f)R_f)}{Z(s)j\omega_{clk}C_C(1+j(\omega_{clk}/\omega_{p2}))} \quad (4)$$

where Z(s) is the impedance of the parallel R-C element. To simplify the transfer function as shown in equation (4), it can be assumed that $g_{m1}Z_{of} \geq 10 A_o$, where $Z_{of}=Z_{o1}\|Z\|R_f$. In typical neural recording applications, $A_o \approx 10^2$. Thus, $g_{m1}Z_{of}$ should be larger than $10^3$. In various embodiments, this can be achieved by using a cascode-stage as the 1st-stage amplifier.

Figure 7:
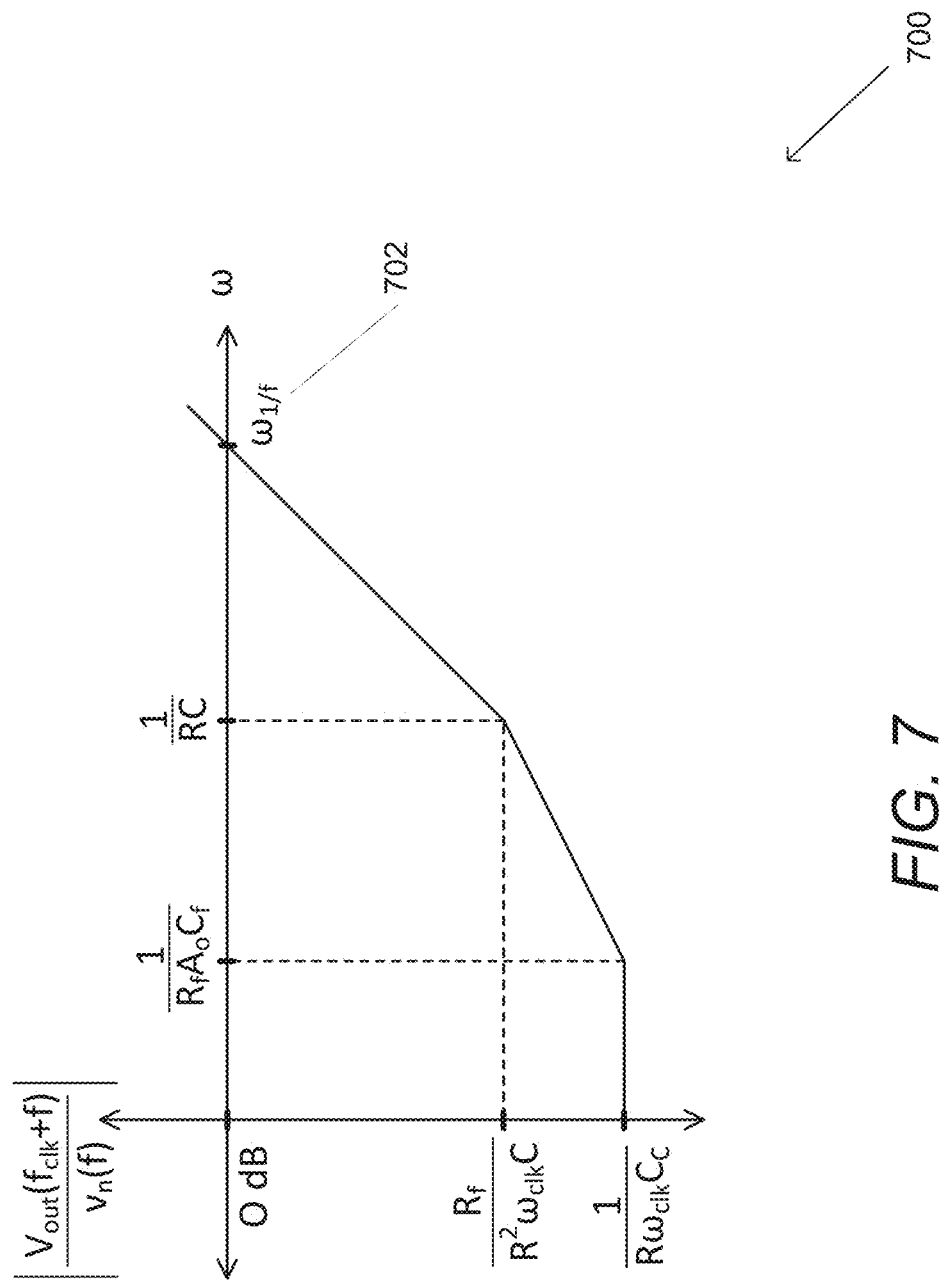
FIG. 7 is a theoretical transfer function in accordance with an embodiment of the invention.

A graph illustrating a transfer function in accordance with an embodiment of the invention is illustrated in FIG. 7. As illustrated in the graph 700, the transfer function $V_{out}/V_n$ from equation (4) is plotted, where the flicker noise corner frequency is denoted by $\omega_{1/f}$ 702. For simplicity, the gain associated with the mixers has been taken to be unity, and $\omega_{p2} \approx \infty$. Flicker noise is attenuated at the output by setting $|V_{out}/V_n|$ at $\omega=\omega_{1/f}$ to be one. This leads to the following constraint $$\frac{\omega_{1/f}C}{\omega_{clk}C_C}\omega_{1/f}A_o C_f R_f \leq 1 \quad (5)$$

The gain from $V_{in}$ 624 to $V_{out}$ 626 should remain unchanged by the addition of a parallel-RC impedance 608 and feedback resistor $R_f$ 614. Therefore, the transfer function from $v_n$ 628 (around $f_{clk}$) to $V_{out}$ 626 (around the baseband frequency) should be the same as a conventional chopper amplifier. To satisfy this condition, the transfer function $V_{out}/v_n$ for $\omega \approx \omega_{clk}$ is is examined, and it is given by $$\frac{V_{out}(s+j\omega_{clk})}{v_n(s)} \approx \quad (6)$$

$$\left(\frac{V_{out}}{v_n}\right)_O \times \left\{\frac{1}{1+\frac{s-s_{clk}}{sC_f R_f g_{m1}}C_C[1+g_{m1}Z_{of}(s_{clk})+s(C_{in}+C_f)R_f]}\right\}$$

where $(V_{out}/v_n)_o$ is the noise gain (=1+$C_{in}/C_f$) in a conventional chopper amplifier. The additional term in equation (6) should be unity to maintain the same signal gain as a conventional chopper amplifier. In various embodiments, the capacitor C 612 is assumed to be a factor of K smaller than $C_c$ 622. In several embodiments, further simplification is enabled by assuming typical values in chopper amplifiers, like $\omega_{clk} \approx 10 \omega_{ugb}$, $C_{in}/C_f \approx 100$, and $C_c \gg 10 C_f$. Using such simplifying assumptions, the additional term in equation (6) is near unity when $$R_f \gg \frac{K}{10\omega_{clk}C_f} \quad (7)$$

For minimal area overhead, the capacitor C 612 can be chosen to be a factor of 10 smaller than $C_c$ 622 (or K=10).

Applying the same assumptions (used to obtain equation (7)) on equation (5), the upper bound on $R_f$ 614 can also be obtained. Thus the range of permissible values for $R_f$ 614 is given by $$\frac{10}{\omega_{clk}C_f} \leq R_f \leq \frac{1000}{\omega_{clk}C_f} \quad (8)$$

In many embodiments, it can be assumed that the flicker noise corner frequency is approximately equal to $\omega_{clk}/100$, which is a typical scenario in a bio-signal amplifier that is not optimized for flicker noise.

If $R_f$ 614 is lower than the minimum bound shown in equation (8), the signal gain reduces, and the input-referred noise increases. If $R_f$ 614 is larger than the maximum bound shown in equation (8), then the flicker noise attenuation can be reduced, thereby allowing more flicker noise to show up as ripples at the output.

In many embodiments, the thermal noise introduced by $R_f$ 614 around the chopping frequency can appear at the amplifier output after being filtered by the capacitor $C_f$ 618. Applying the assumptions used to obtain equation (8), the output noise PSD (around baseband) due to $R_f$ 614 is given by $$v_{n,Rf}^2 \approx v_{n,gm1}^2\left[\frac{1}{10\gamma\omega_{clk}C_f R_f}\right] \quad (9)$$

where $v_{n,gm1}$ is the thermal noise PSD due to $g_{m1}$ 602, which is the dominant noise source in a conventional chopped amplifier. From equations (8)-(9), and assuming it can be seen that the noise power contribution from $R_f$ 614 is at least a factor of $10^2$ lower than the noise contribution of $g_{m1}$ 602, thus making it negligible. In various embodiments, the thermal noise introduced by R 610 around the chopping frequency and its harmonics are shorted by the capacitor C 612, and doesn't appear at the output.

In various embodiments, for a bio-signal amplifier recording LFP and action potentials, the amplifier bandwidth can be around 10 kHz. This sets $f_{clk}$ 630 to about 100 kHz. For $C_f$=0.1 pF, the range of permissible values for $R_f$ 614 can be 160 MΩ to 16 GΩ (from equation (8)). For a ripple-reduction of 80 dB and for $g_{m1}$≈10 µA/V, the resistor R 610 should be larger than 1 GΩ. Hence, in many embodiments, $R_f$ 614 and R 610 need not be accurately set, but such large resistors can be difficult to realize using passive metal or poly structures. MOS devices biased in weak inversion have large resistance, but are difficult to set accurately, and are very nonlinear when subjected to large signal swings. In the ripple-rejection techniques in accordance with embodiments of the invention, the large resistors R 610 and $R_f$ 614 can be placed inside the feedback loop, where the signal swings are much smaller than the amplifier output swings. Thus, the nonlinearity of the large resistors should not pose a problem. And as discussed above, R 610 and $R_f$ 612 need not be accurately set, thus making the use of MOS based resistors a feasible approach.

Figure 8:
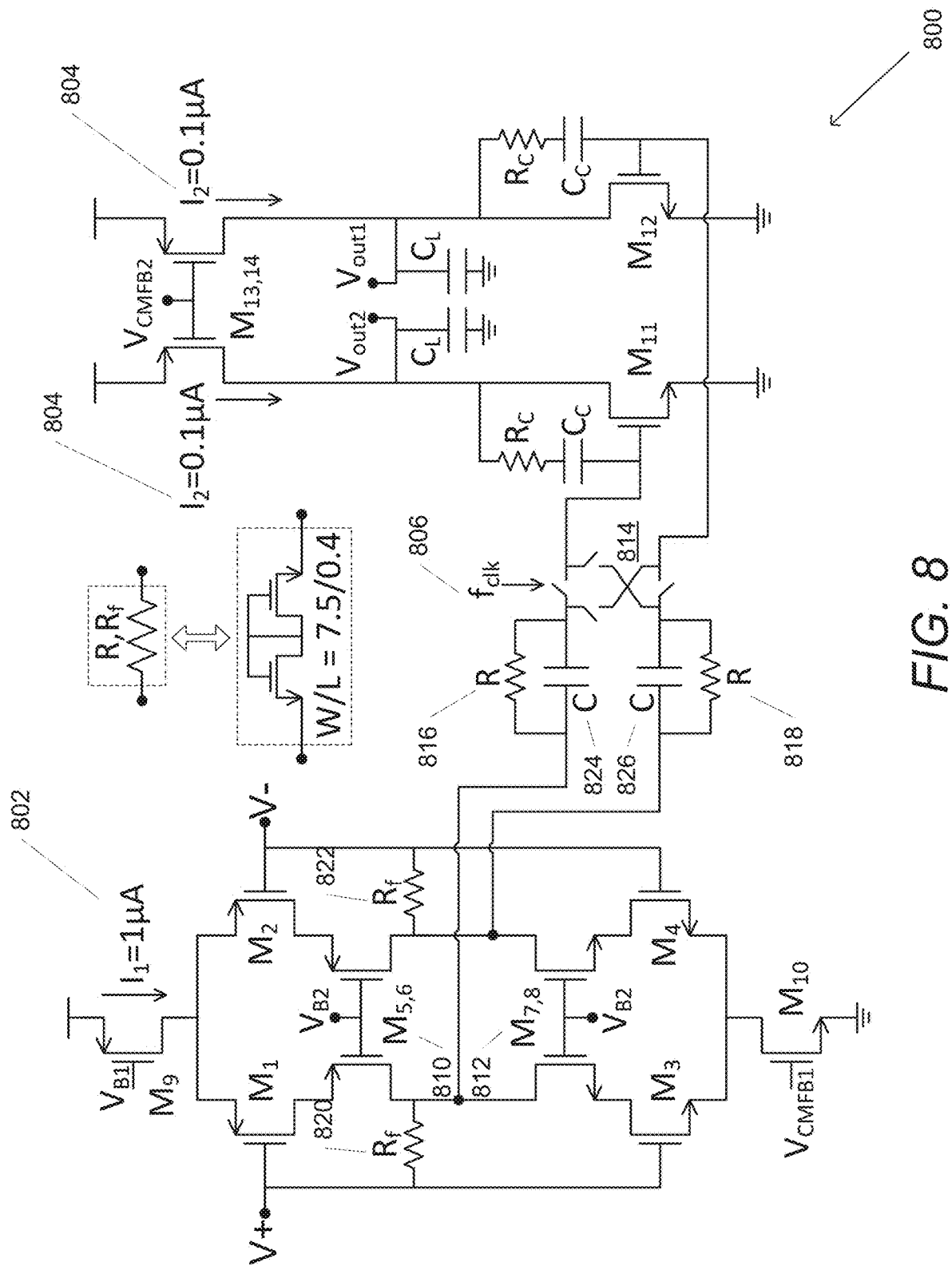
FIG. 8 is a schematic diagram of an amplifier with RR in accordance with an embodiment of the invention.

A chopper-stabilized bio-signal amplifier in accordance with many embodiments of the invention can be designed and simulated using a 65 nm CMOS process. An amplifier schematic in accordance with an embodiment of the invention is illustrated in FIG. 8. In many embodiments, the transistor sizes and operating points, along with the values of the passive elements that can be utilized in the schematic 800 are shown in Table II (reproduced below). In various embodiments, the supply can be set at 1.2V and the total bias-currents in the first 802 and second stages 804 at 1 µA and 0.2 µA respectively. In several embodiments, the closed-loop gain is set to 50, and the chopping frequency $f_{clk}$ 806 is set to 50 kHz. In a variety of embodiments, low-VT devices were used for the cascode transistors $M_5$-$M_8$ 810, 812, and thick-oxide devices were used for all other transistors. In further embodiments, the passive mixers can be realized using transmission gates 814, with a maximum ON-resistance of 2 kΩ. In many embodiments, the large resistors R 816, 818 and $R_f$ 820, 822 can be realized using thin-oxide NMOS devices and the capacitors C 824, 826 were chosen to be $C_c$/8, minimizing additional chip area.

TABLE II

OPERATING POINTS FOR AMPLIFIER SHOWN IN FIG. 8

| Devices | W/L | $g_m$(µA/V) | $g_m/I_D$ |
|---|---|---|---|
| $M_{1,2}$ | 50/0.5 | 12.4 | 24.8 |
| $M_{3,4}$ | 50/0.5 | 13.9 | 27.8 |
| $M_{5,6}$ | 10/0.1 | 12.8 | 25.6 |
| $M_{7,8}$ | 10/0.1 | 14.0 | 28 |
| $M_9$ | 50/0.5 | 23.6 | 23.6 |
| $M_{10}$ | 10/6.5 | 15.2 | 15.2 |
| $M_{11,12}$ | 3/20 | 1.55 | 15.5 |
| $M_{13,14}$ | 20/10 | 1.72 | 17.2 |
| Passives | | | |
| R | 1 GΩ | $C_C$ | 8 pF |
| $R_f$ | 1 GΩ | $C_{in}$ | 5 pF |
| $R_C$ | 300 kΩ | $C_f$ | 0.1 pF |
| C | 1 pF | $C_{load}$ | 4 pF |

Although specific CSAs with RR are discussed above with respect FIGS. 6-8 and Table II, any of a variety of CSAs with RR as appropriate to the requirements of a specific application can be utilized in accordance with embodiments of the invention. Characteristics of CSAs with RR in accordance with embodiments of the invention are further discussed below.

Characteristics of Amplifiers with Ripple-Rejection

Figure 9:
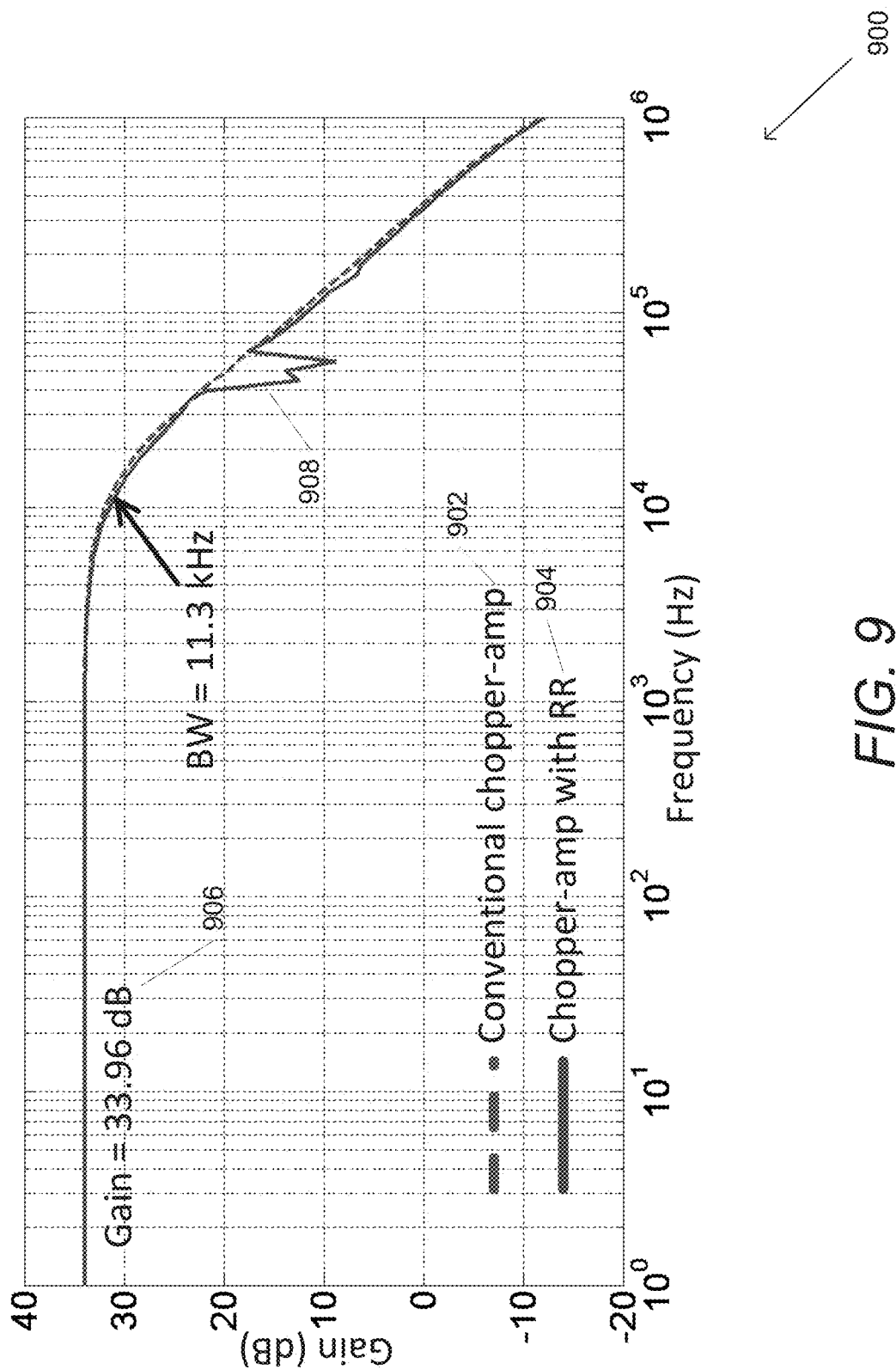
FIG. 9 is a graph illustrating simulated gain of an amplifier with RR in accordance with an embodiment of the invention.

A graph illustrating simulated gain of a conventional CSA and a CSA with RR in accordance with an embodiment of the invention is illustrated in FIG. 9. The graph 900 illustrates gain of a convention CSA 902 and also gain of a CSA with RR 904 in accordance with an embodiment of the invention. As can be seen, the gains of the two amplifiers are nearly identical at 33.96 dB 906 except around the chopping frequency $f_{clk}$ where a notch 908 in the gain plot of FIG. 9 is observed around $f_{clk}$ when RR is used.

Figure 10:
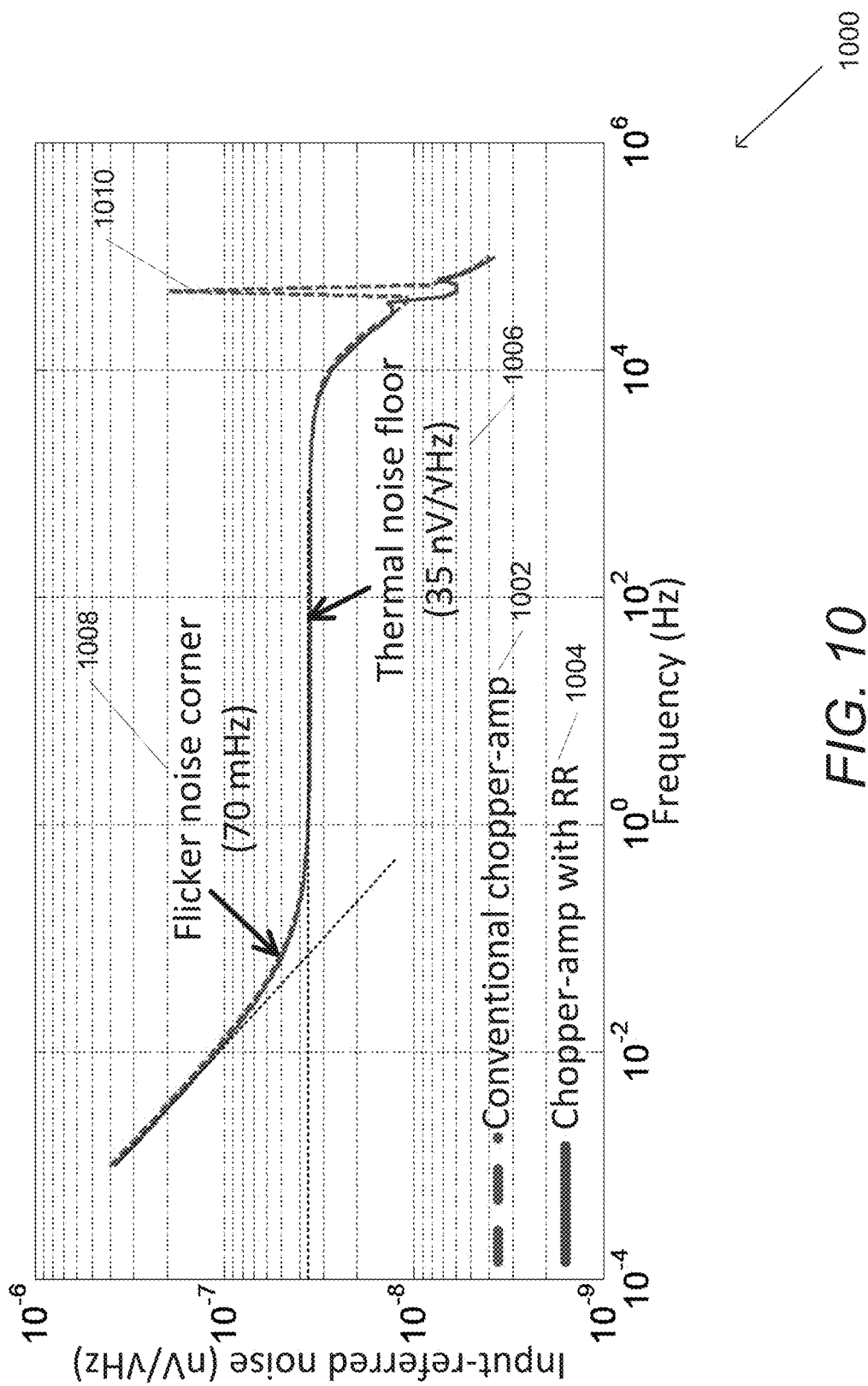
FIG. 10 is a graph illustrating simulated noise of an amplifier with RR in accordance with an embodiment of the invention.

A graph illustrating simulated noise of a conventional CSA and a CSA with RR in accordance with an embodiment of the invention is illustrated in FIG. 10. The graph 1000 illustrates the input-referred noise for a conventional CSA 1002 and the input-referred noise for a CSA with RR 1004 in accordance with an embodiment of the invention. The graph illustrates similar values for both the amplifiers having a thermal noise density of 35 nV/√Hz, 1006 and a flicker noise corner frequency of 70 mHz 1008. However, the up-converted flicker noise peak 1010 is absent around $f_{clk}$ when RR is used, showing the effectiveness of the RR technique. In various embodiments, any input signal at $f_{clk}$ can be demodulated to baseband when seen by $g_{m1}$, and is made indistinguishable from low-frequency flicker noise or offset of $g_{m1}$. Thus, any input signal at $f_{clk}$ is typically blocked by the RR technique.

Figures 11A, 11B:
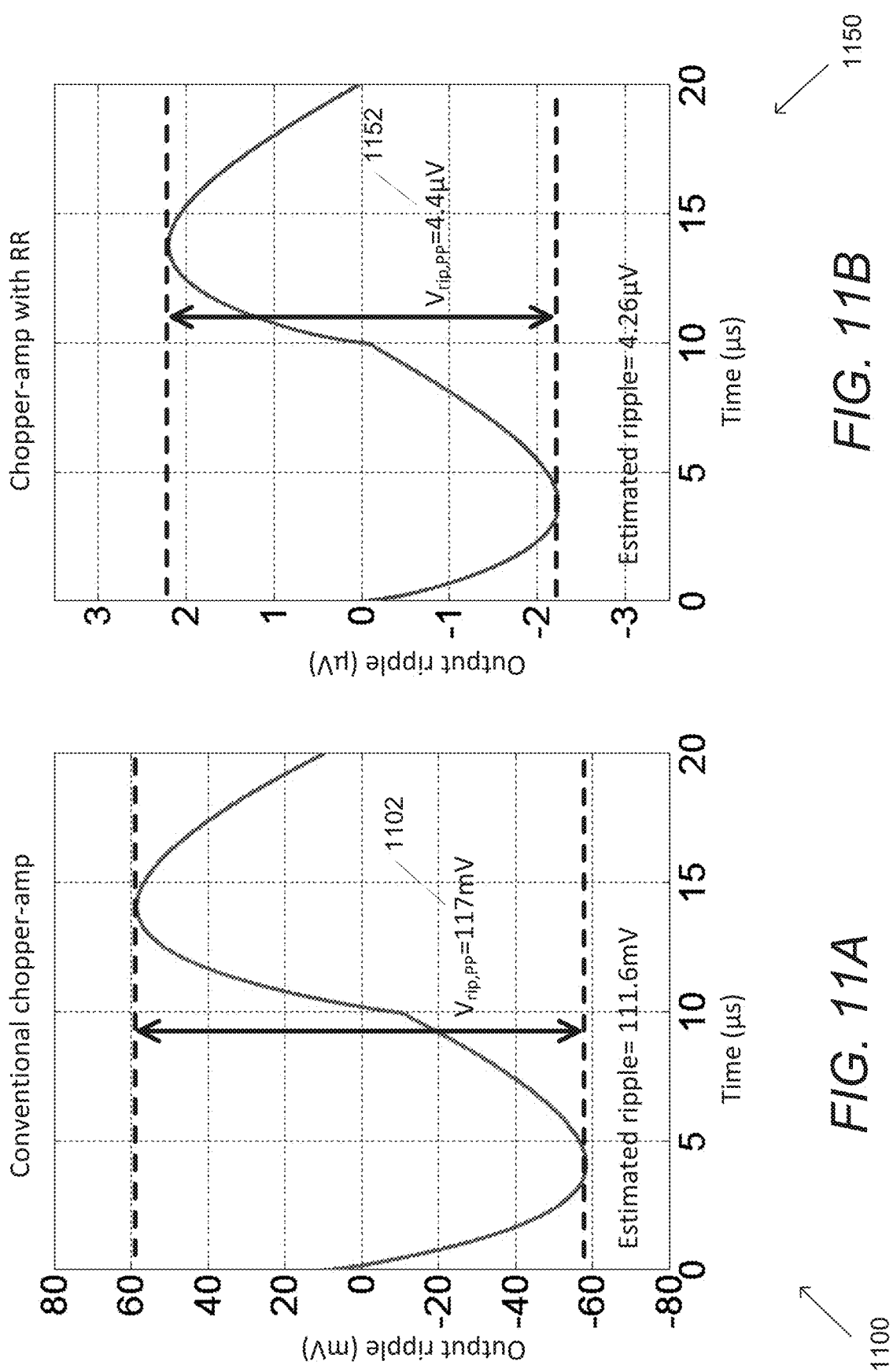
FIGS. 11A-B are graphs illustrating simulated output-ripple for a conventional CSA and a CSA with RR, respectively, in accordance with an embodiment of the invention.

Graphs illustrating a transient simulation performed with an input offset of 5 mV in accordance with an embodiment of the invention are illustrated in FIGS. 11A-B. The graph 1100 shows the output ripple of a convention CSA. As can be seen, the output-ripple 1102 is observed to be 117 m$V_{pp}$. In contrast, graph 1150 shows the output ripple of a CSA with RR in accordance with an embodiment of the invention. Here, the output-ripple 1152 is observed to be 4.4 µ$V_{pp}$, which corresponds to a ripple-attenuation of 88 dB. The estimate of the ripple utilizing equations (2)-(3) is 111.6 m$V_{pp}$ (without RR) and 4.26 µ$V_{pp}$ (with RR), which aligns with the simulation results as shown in FIGS. 11A-B. In many embodiments, due to the finite-bandwidth of the 2nd stage ($g_{m2}$), the ripples can appear like a sine wave rather than a saw-tooth wave.

Figure 12:
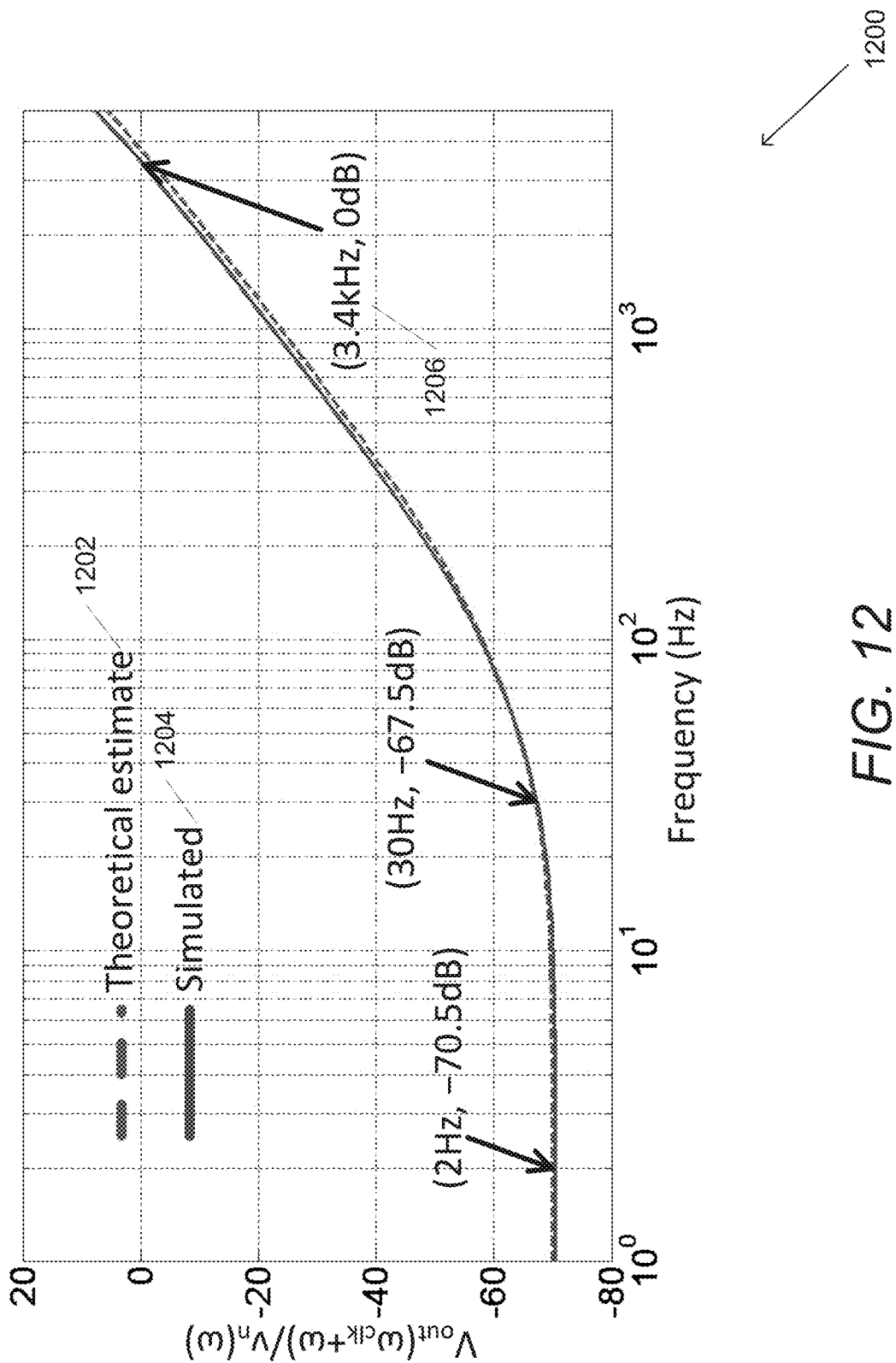
FIG. 12 is a graph illustrating theoretical and simulated transfer functions in accordance with an embodiment of the invention.

To verify the effectiveness of the RR technique in reducing output ripple due to flicker noise, the transfer function from $v_n(f)$ to $V_{out}(f)$ can be simulated. A graph illustrating the theoretical and simulated transfer functions in accordance with an embodiment of the invention is illustrated in FIG. 12. In many embodiments, the theoretical estimate can be defined using equation (4). The graph 1200 illustrates the theoretical estimate 1202 and the simulated 1204 transfer functions. As can be seen, the theoretical estimate is in close agreement with the simulation, and the low-frequency noise below 3.4 kHz is attenuated 1206.

Figure 13:
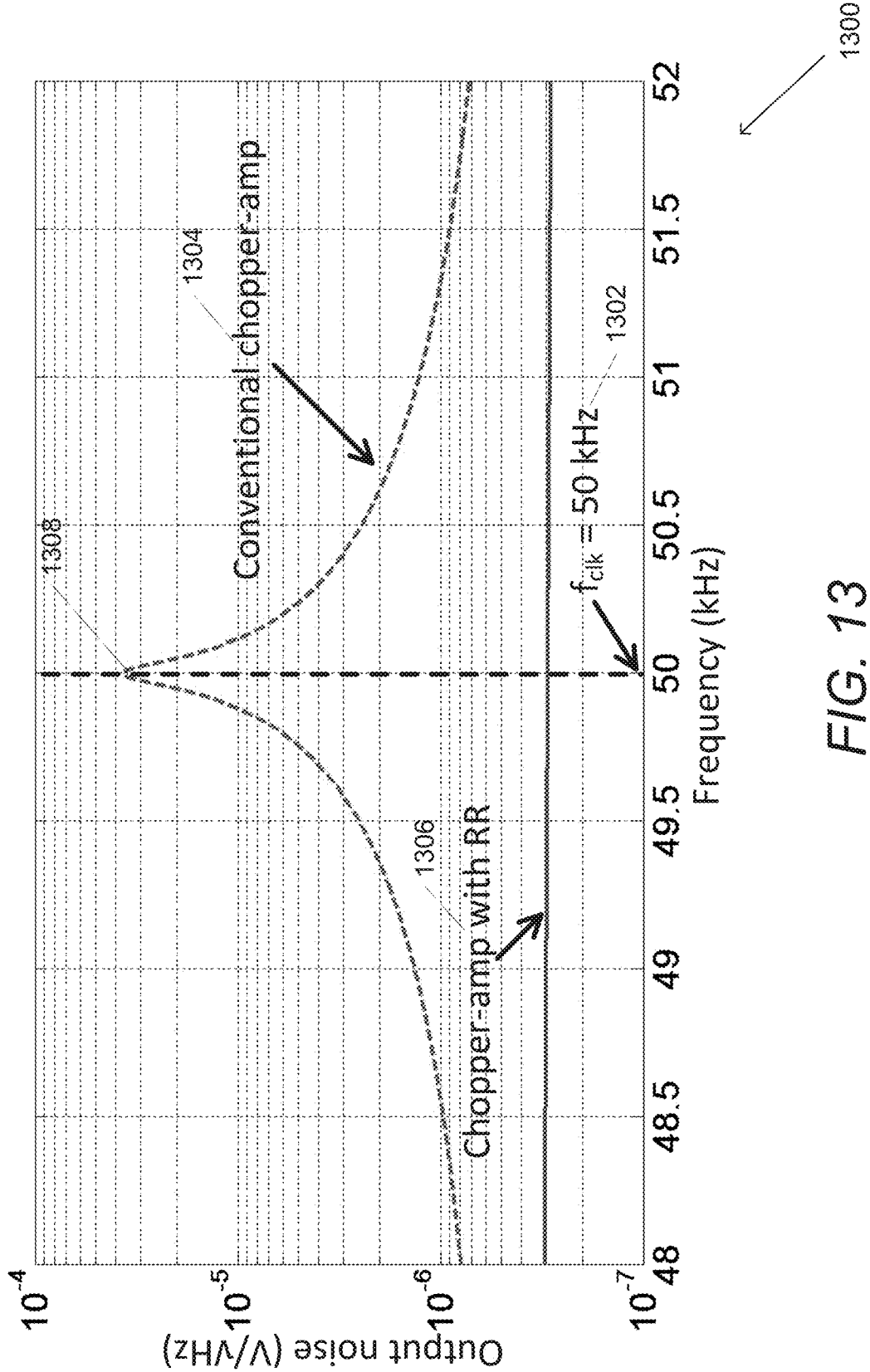
FIG. 13 is a graph illustrating output noise in accordance with an embodiment of the invention.

A graph illustrating output noise around $f_{clk}$ in accordance with an embodiment of the invention is illustrated in FIG. 13. The graph 1300 illustrates the output noise around few 1302 for a conventional CSA 1304 and a CSA with RR 1306 in accordance with an embodiment of the invention. In many embodiments, the peak due to up-converted flicker noise 1308 is absent when the RR technique is used, thus showing the effectiveness of the RR technique in suppressing flicker noise.

In various embodiments, a transient simulation can be performed with an input tone at 1 kHz and an input amplitude of 8 m$V_{pp}$. In several embodiments, the THD at the output is −91 dB when the nonlinear resistor (as illustrated in FIG. 8) was used for R and $R_f$, and −97 dB when the nonlinear resistors were replaced with ideal resistors. Thus, in various embodiments, the nonlinear resistors can limit the THD to −91 dB, which can be sufficient for many bio-signal amplifiers.

In Table III (reproduced below) a CSA with RR in accordance with an embodiment of the invention is compared with published conventional designs A, B, and C. In various embodiments, the overall performance of the amplifier with RR in accordance with an embodiment of the invention is on par or better than the published designs. The ripple-rejection performance comparison shows that the CSA with RR in accordance with an embodiment of the invention achieves larger ripple-reduction for a nominal area increase, and consumes no additional power.

TABLE III

COMPARISON WITH STATE-OF-THE-ART CHOPPER AMPLIFIERS

| Specification | A | B | C | CSA with RR |
|---|---|---|---|---|
| Overall performance | | | | |
| Supply (V) | 1 | 1.5 | 1.8 | 1.2 |
| Current (μA) | 1.8 | 194 | 13 | 1.2 |
| Gain (dB) | 40 | >30 | >0 | 34 |
| Bandwidth (Hz) | 700 | 320k* | 3.5k* | 11.3k |
| Inp. Noise (nV/√Hz) | 60 | 13.5 | 55 | 35 |
| NEF | 3.3 | 7.2 | 8.1 | 1.7 |
| Technology | 65 nm | 0.18 μm | 0.6 μm | 65 nm |
| Ripple-rejection performance | | | | |
| Ripple-reduction (dB) | 50 | 28 | 54 | 88 |
| Additional cap (pF) | 8.3 | None | 32 | 2 |
| Additional current (μA) | 0.105 | 2 | None | None |

*Estimate for closed-loop gain of 40 dB

Although specific characteristics of amplifiers with RR are discussed above with respect to FIGS. 9-13 and Tables II-III, any of a variety of amplifiers with RR having specific characteristics as appropriate to the requirements of a specific application can be utilized in accordance with embodiments of the invention. Processes for utilizing a DC-servo loop having duty-cycled resistors for high-pass filtering of electrode DC offset in accordance with embodiments of the invention are discussed further below.

DC-Servo Loop for HP Corner Using "Duty-Cycled" Resistors

Figure 14:
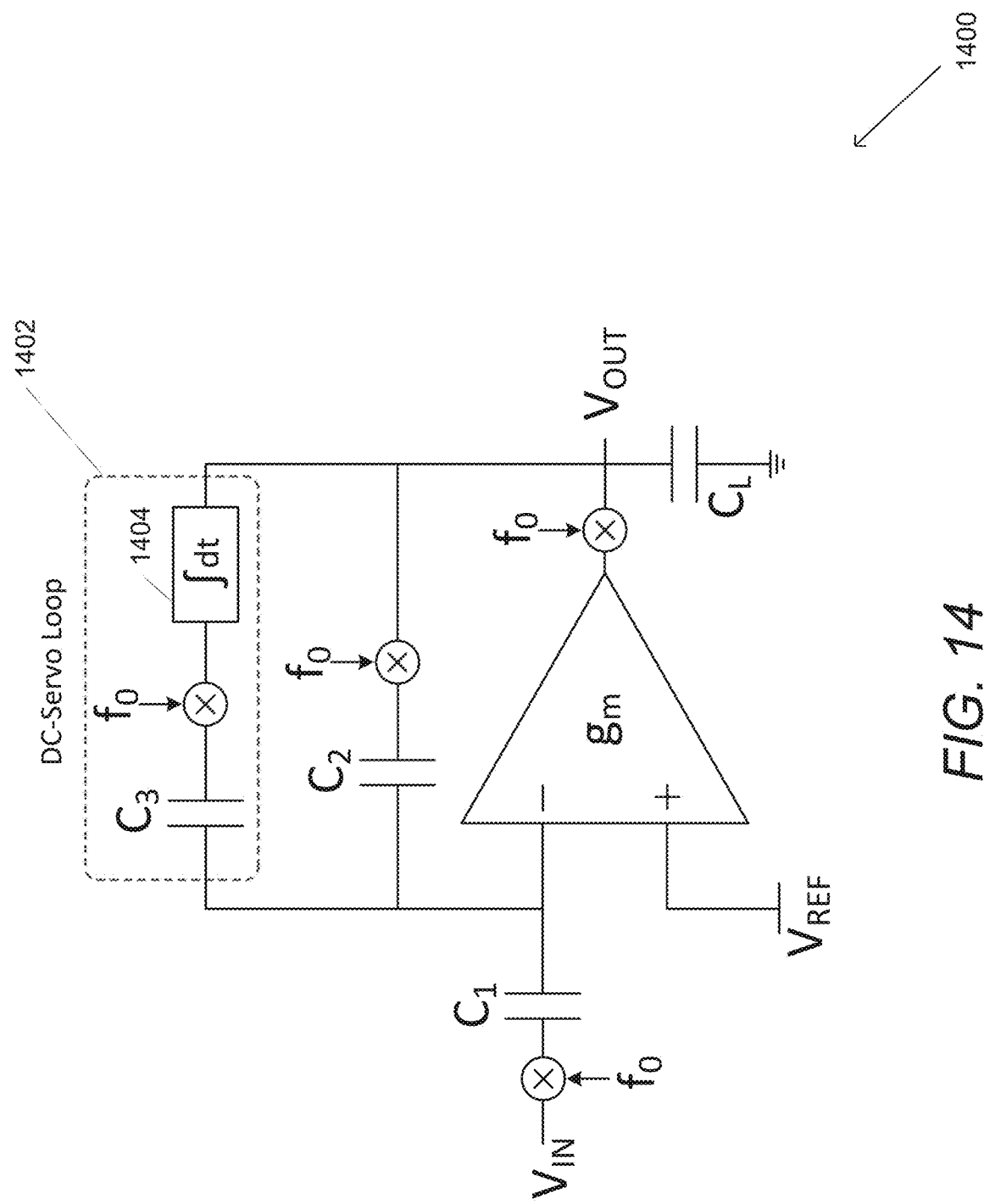
FIG. 14 is a schematic diagram illustrating a CSA with a DC servo-loop in accordance with the prior art.

To attenuate the electrode DC offset, prior designs have used a DC servo loop, where negative feedback is employed to null the output signal at very-low frequencies. A schematic of a conventional CSA with a DC servo loop in accordance with the prior art is shown in FIG. 14. As illustrated in 1400, the chopper-amplifier can include a DC-servo loop 1402 that includes an integrator 1404. The integrator 1404 in the servo loop 1402 sets the loop bandwidth of the feedback loop. To ensure that the signal of interest is not attenuated at the output, the loop bandwidth of the servo loop should be less than the lower edge of the signal band of interest (~1 Hz). Thus, such a configuration would typically call for a very-low bandwidth integrator.

Prior designs have utilized switched-capacitor integrators with very-large capacitors (~1 nF) to realize the low bandwidth. Other designs have proposed switched-capacitor techniques with reduced capacitor ratios to realize the integrator with significantly lower capacitance values. However, these implementations can significantly increase the noise contribution of the integrators in the signal band. For example, a proposed design using a switched-capacitor technique to realize the servo loop resulted in an input-referred noise of the recording front-end increasing from 0.7 $\mu V_{rms}$ to 6.7 $\mu V_{rms}$ in the LFP band (0.5 Hz-100 Hz). To keep this noise low, the design calls for ~1 nF capacitance, which would significantly increase the required chip area.

Figure 15A:
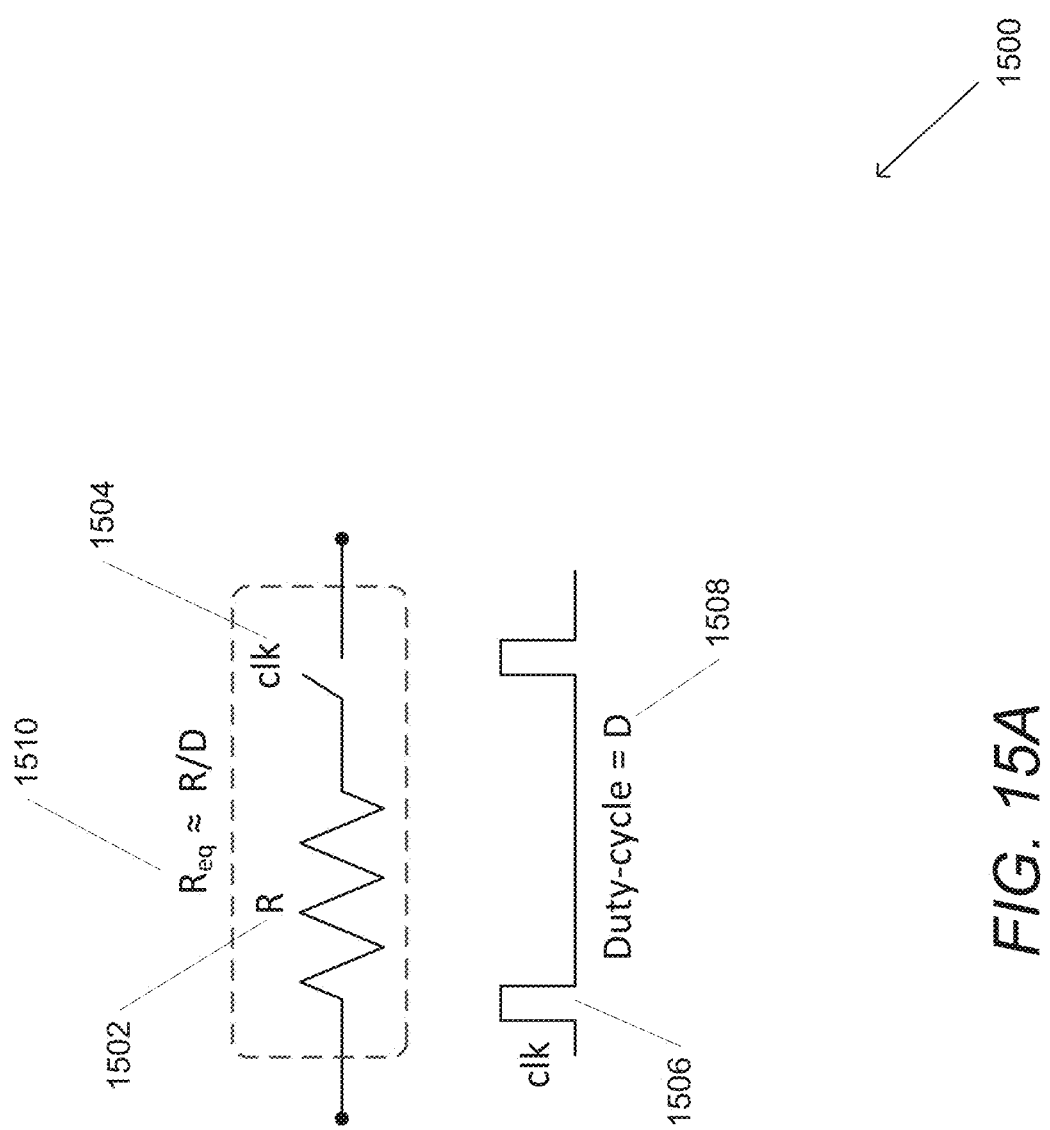
FIG. 15A is a schematic diagram illustrating a duty-cycled resistor in accordance with an embodiment of the invention.

Although pseudo-resistors may be used as large resistors in a feedback network, as discussed above, their nonlinearity and extreme sensitivity to process and temperature make them unsuitable. However, "duty-cycled" resistors could realize large resistor values in the range of several GΩ by using linear passive resistors of ~1 MΩ and simple switches. A schematic diagram illustrating a duty-cycled resistor in accordance with an embodiment of the invention is shown in FIG. 15A. The diagram 1500 illustrates a resistor R 1502 that can be periodically removed from the circuit by opening the series switch 1504. The switch 1504 is closed for a period of DT, where T is the time period of the control clock 1506, and D is the duty-cycle of the clock 1508. On average, the value of the resistance R is amplified to $R_{eq}$=R/D 1510.

Figure 15B:
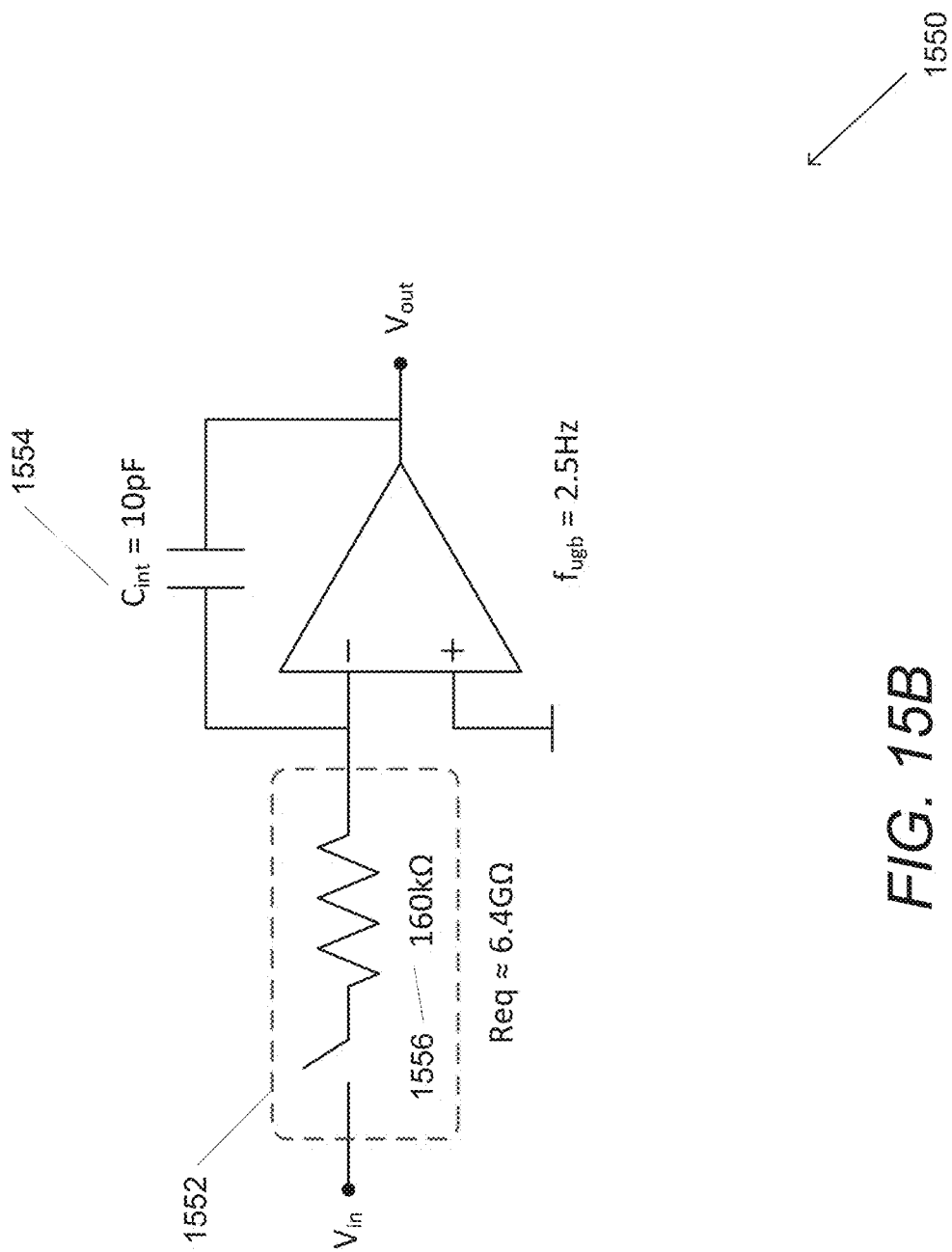
FIG. 15B is a schematic diagram illustrating an op-amp based integrator using a duty-cycled resistor in accordance with an embodiment of the invention.

By using advanced technology nodes like 40 nm, it is possible to create voltage pulses on the order of 1 ns. Given that the chopping period is 40 μs, it is possible to realize clock waveforms with duty-cycles of about 1/40000. A schematic diagram illustrating an op-amp-based integrator using a duty-cycled resistor in accordance with an embodiment of the invention is shown in FIG. 15B. As illustrated in 1550, an op-amp based integrator can be implemented using the duty-cycled resistor 1552 to realize a 6.4 GΩ resistance. With passive elements such as (but not limited to) a 10 pF capacitor 1554 and a 160 kΩ passive resistor 1556, an integrator with a unity-gain bandwidth of 2.5 Hz can be realized. In many embodiments, the $T_{on}$ can equal 2 ns, $f=f_{chop}/2$=12.5 kHz, and D=1/40000.

Figure 16:
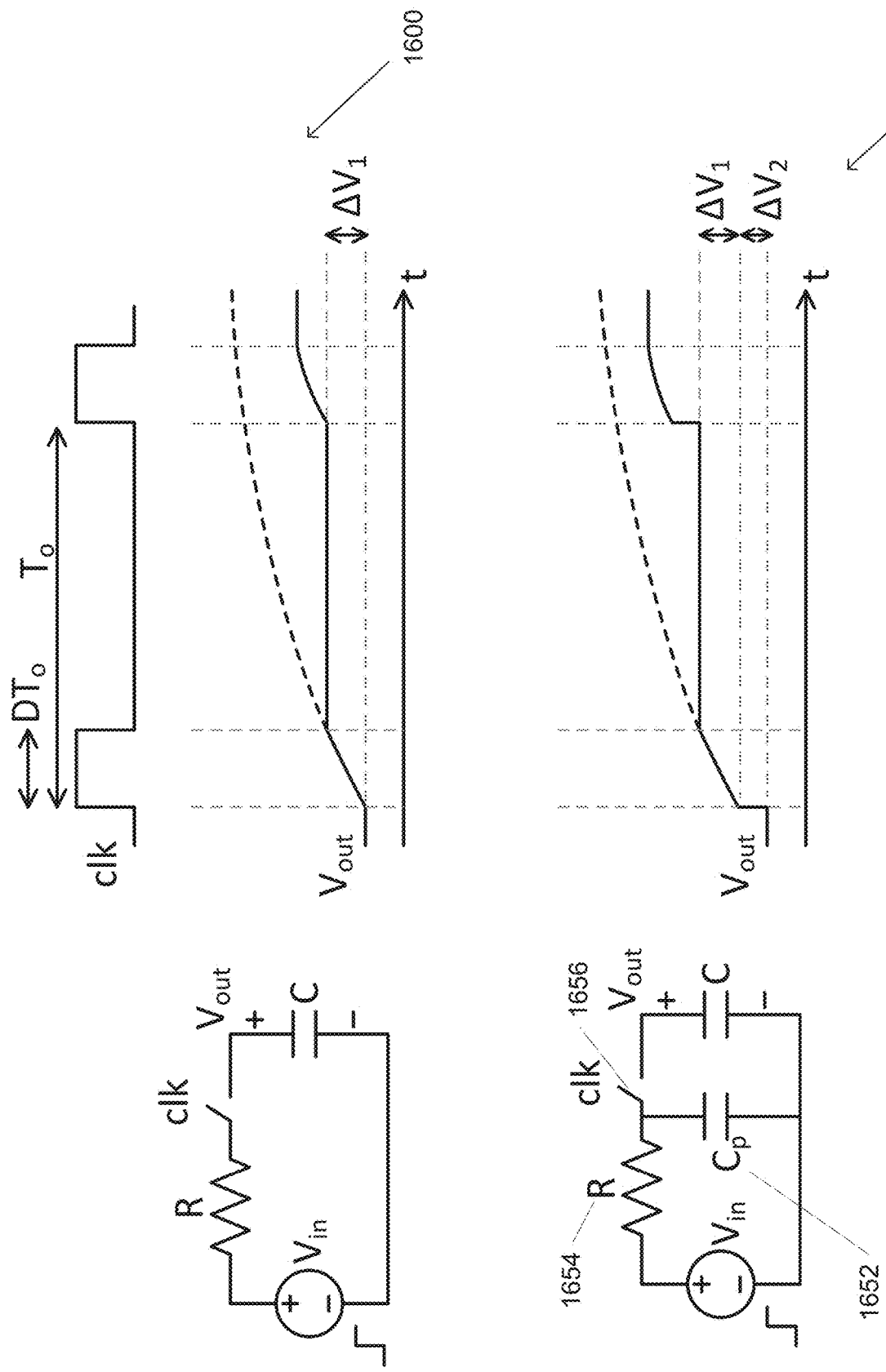
FIG. 16 are plots illustrating limitations of duty-cycled resistors in accordance with the prior art.

Unlike switched-capacitor integrators, the noise associated with duty-cycled resistors behave in line with traditional resistors with a resistance value equal to the amplified resistance. Thus the noise of the duty-cycled resistor can be pushed to low frequencies, and the in-band noise contribution of the duty-cycled resistors can be kept low. Time-domain plots illustrating characteristics of duty-cycled resistors in accordance with an embodiment of the invention are illustrated in FIG. 16. The time-domain plot 1600 illustrates an ideal behavior whereas the time-domain plot 1650 illustrates the effect of a parasitic capacitor $C_p$ 1652. The maximum realizable resistance $R_{max}$ is limited by the parasitic capacitance $C_p$ 1652 between the resistor R 1654 and the series switch 1656, as this parasitic capacitor will act like a shunt switched capacitor resistance. In many embodiments, the $R_{max}$ is equal to the inverse of $C_p$ times $f_{clk}$.

Figure 17:
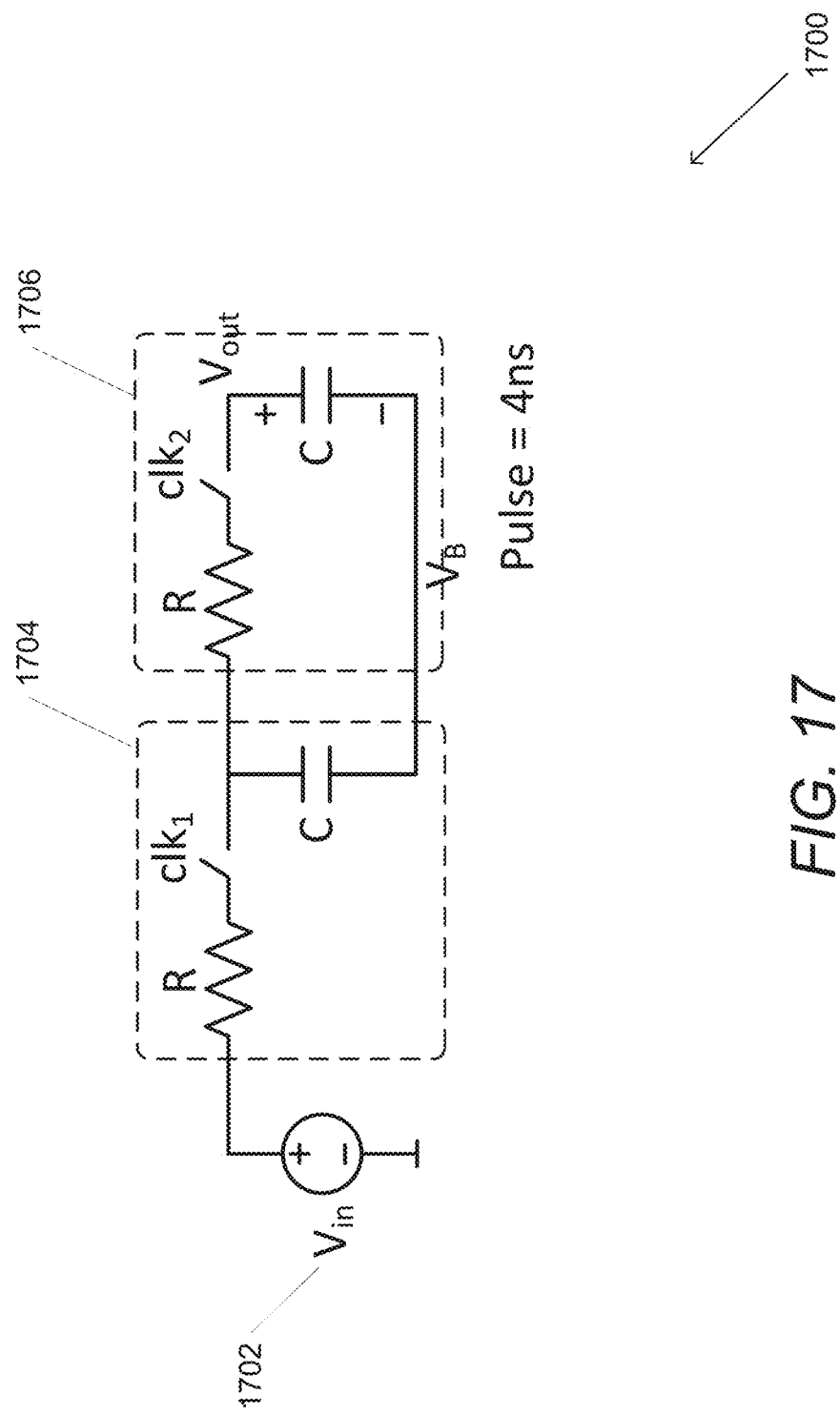
FIG. 17 is a schematic diagram illustrating a multi-rate approach using duty-cycled resistors in accordance with an embodiment of the invention.

To solve issues related to limited resistance due to the parasitic capacitors as discussed above, a multi-rate approach using duty-cycled resistors can be implemented. A multi-rate configuration using duty-cycled resistors in accordance with an embodiment of the invention is illustrated in FIG. 17. In the multi-rate approach 1700, the input signal 1702 can be low-pass filtered using an anti-alias filter 1704. In many embodiments, the filtered signal can be applied to a low-pass filter 1706 that operates at a much lower frequency ($f_2$) than the Nyquist frequency of the input signal. Since the switching frequency is reduced, the shunt resistance formed by the parasitic capacitor $C_p$ is much larger, and will not limit the maximum realizable resistance. In several embodiments, utilizing a $f_1$=25 kHz, $f_2$=(1/32)$f_1$, R=100 kΩ, C=2 pF, and a low-pass BW=3.4 Hz, a 23 GΩ resistance was realized using very nominal values for passive elements.

Although specific process for utilizing a DC-servo loop having duty-cycled resistors for high-pass filtering are discussed above with respect to FIGS. 14-17, any of a variety of DC-servo loop configurations using duty-cycled resistors for high-pass filtering as appropriate to the requirements of a specification application can be utilized in accordance with embodiments of the invention. The use of multi-rate duty-cycled resistors to realize large, linear resistors is not limited to DC-Servo loops, and can be used in any application that requires large linear resistors within a small area. Implementations of a high dynamic range front-end for neural signal recording systems in accordance with embodiments of the invention are discussed further below.

Complete Implementation of the CCIA

Figure 18A:
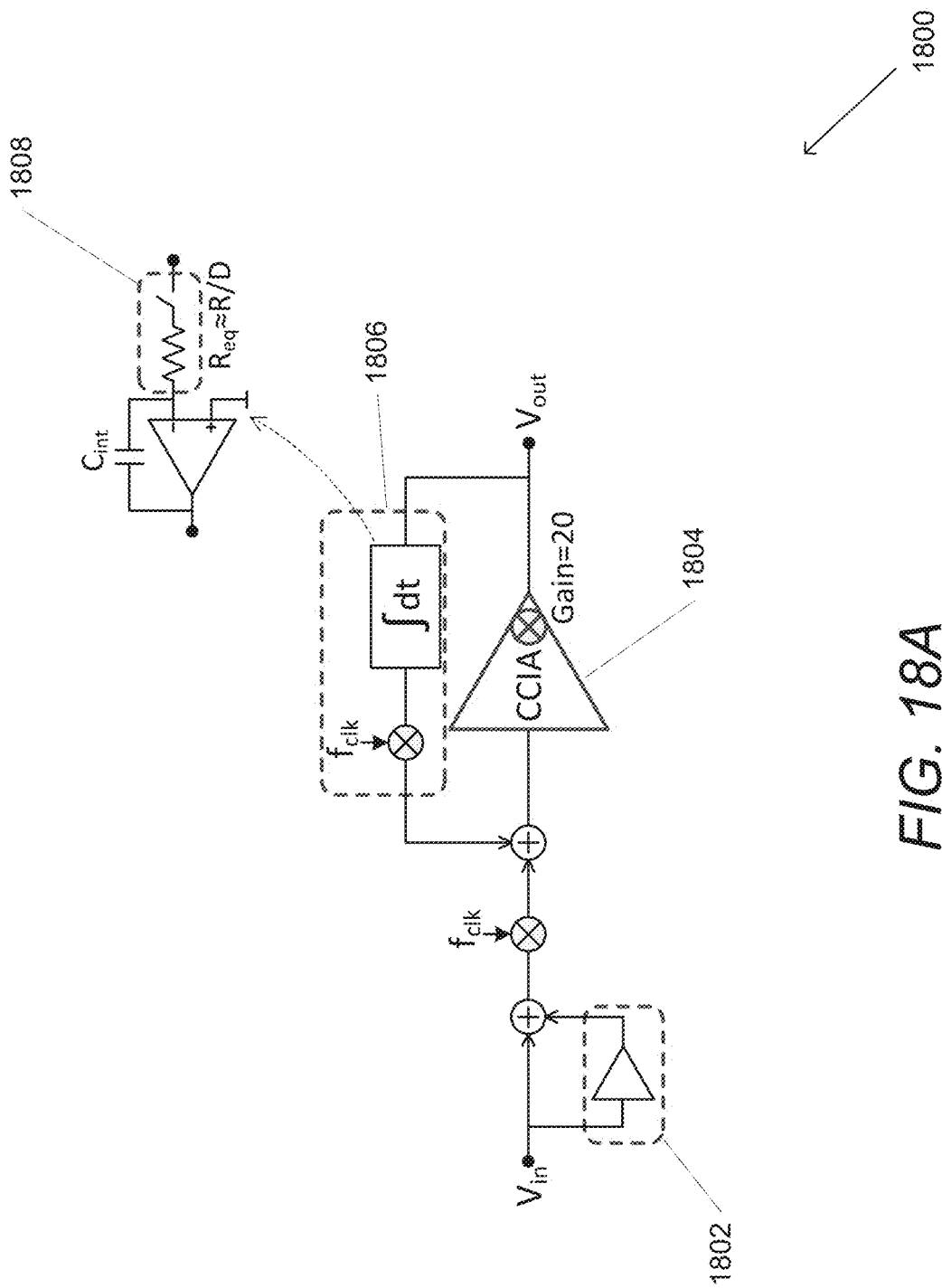
FIG. 18A is a schematic diagram illustrating a block-level implementation of a complete Capacitive-coupled Chopper-Stabilized Instrumentation Amplifier (CCIA) in accordance with an embodiment of the invention.

A high dynamic range sensing front-end for neural signal recording systems can be implemented using a capacitive-coupled chopper-stabilized instrumentation amplifier (CCIA) utilizing the various techniques described above. A block-level implementation of the CCIA in accordance with an embodiment of the invention is illustrated in FIG. 18A. The CCIA 1800 can include an auxiliary path 1802 configured to pre-charge capacitors for boosting input impedance as described above. Further, the CCIA can utilize a CSA with RR 1804 that utilizes a parallel-RC impedance circuit as described above. In addition, the CCIA can include a DC-Servo loop 1806 for high-pass filtering electrode DC offsets utilizing a duty-cycled resistor 1808 as described above.

Figure 18B:
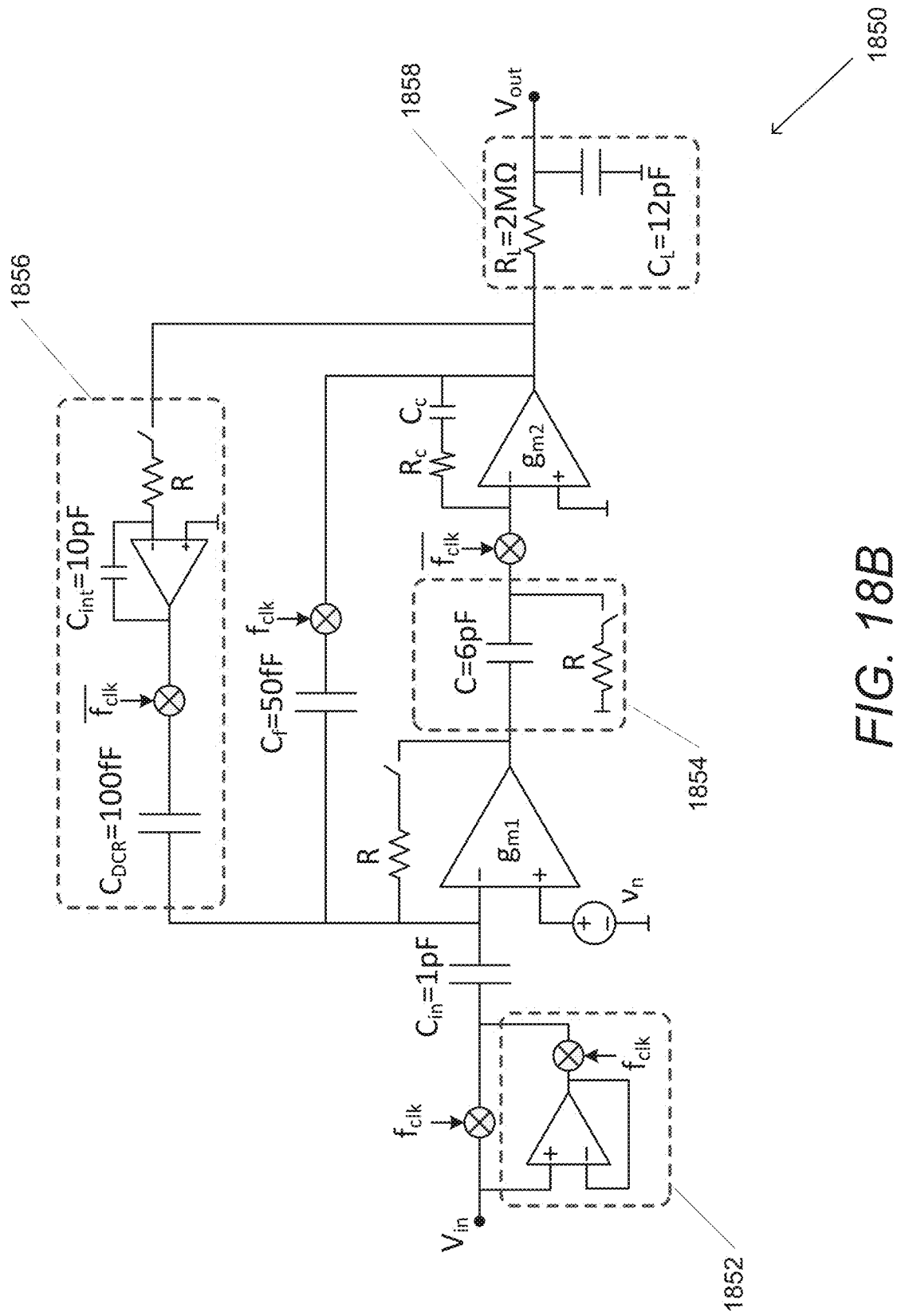
FIG. 18B is a schematic diagram illustrating a circuit-level implementation of a CCIA in accordance with an embodiment of the invention.

A circuit-level implementation of the CCIA in accordance with an embodiment of the invention is illustrated in FIG. 18B. The CCIA 1850 can include an auxiliary path 1852 configured to pre-charge capacitors for boosting input impedance as described above. Further, the CCIA can utilize a CSA with RR 1854 that utilizes a parallel-RC impedance circuit as described above. In addition, the CCIA can include a DC-Servo loop 1856 for high-pass filtering electrode DC offsets utilizing a duty-cycled resistor as described above. Moreover, the CCIA can also include an anti-alias filter 1858 as described above. In many embodiments, the CCIA amplifier can be designed utilizing various CMOS processes including (but not limited to) a 40 nm CMOS process.

Experimental results and validation of the CCIA in accordance with an embodiment of the invention are presented in TABLE IV (reproduced below). Table IV summarizes the performance of the CCIA utilizing the various techniques described above, and compares it to the conventional designs. As can be readily appreciated, the embodiments of the invention significantly improve upon the peak input-swing, DC input impedance, linearity and dynamic range, while having comparable power and noise performance.

TABLE IV

| | COMPARISON WITH STATE-OF-THE-ART FRONT-ENDS | | | | |
|---|---|---|---|---|---|
| Spec | X | W | Y | Z | CCIA |
| Power/Ch | 2 µW | 1.8 µW | 5.04 µW | 2.3 µW | 2 µW |
| Supply | 1.8 V | 1 V | 0.5 V | 0.5 V | 1.2 V |
| Signals [a] | LFP | LFP | AP + LFP | LFP | AP + LFP |
| Peak Input | 5 mV$_p$ | Not specified | Not specified | 0.5 mV$_p$ | 20 mV$_p$ |
| Input-referred noise (V$_{rms}$) | LFP: 1 µV | LFP: 6.7 µV [b] | AP: 4.7 µV LFP: 4.3 µV | AP: 1.3 µV LFP: 1.3 µV | AP: 7 µV LFP: 2 µV |
| DC Z$_{in}$ | 8 MΩ | 6 MΩ [b] | ∞ | 28 MΩ | >300 MΩ |
| Dynamic Range | 64 dB (LFP) | — | 50 dB | 51 dB (LFP) | 69 dB (AP) 78 dB (LFP) |
| Total Harmonic Distortion (THD) | −60 dB | Not specified | −35 dB | −48 dB | −74 dB |

[a] LFP: Local Field Potentials, AP: Action Potentials
[b] Servo-Loop enabled
[c] Calculated for distortion power = noise power Although specific implementations for a high dynamic range sensing front-end using a CCIA are discussed above with respect to FIGS. 18A-B and Table IV, any of a variety of implementations utilizing the above discussed techniques can be utilized for a high dynamic range sensing front-end in accordance with embodiments of the invention. While the above description contains many specific embodiments of the invention, these should not be construed as limitations on the scope of the invention, but rather as an example of one embodiment thereof. It is therefore to be understood that the present invention may be practiced otherwise than specifically described, without departing from the scope and spirit of the present invention. Thus, embodiments of the present invention should be considered in all respects as illustrative and not restrictive.

What is claimed is:

1. A bio-signal amplifier comprising:
   an input signal comprising an input voltage and an input current, where the input signal is modulated to a predetermined chopping frequency;
   a first amplifier stage comprising a first input configured to receive the modulated input signal and generate a first output, where the first output comprises an offset current and a portion of the modulated input current;
   a parallel-RC circuit connected to the first amplifier stage and configured to receive the first output and generate a parallel-RC circuit output by selectively blocking the offset current utilizing at least one RC resistor and at least one RC capacitor;
   a second amplifier stage connected to the parallel-RC circuit comprising a second input configured to receive the parallel-RC circuit output and generate a second output, where the second output is an amplified version of the input signal with ripple-rejection.

2. The bio-signal amplifier of claim 1, further comprising an auxiliary path configured for boosting input impedance by pre-charging at least one input capacitor.

3. The bio-signal amplifier of claim 2, wherein the auxiliary path is set to an enable configuration by connecting the at least one input capacitor to an auxiliary path buffer.

4. The bio-signal amplifier of claim 3, wherein the auxiliary path is set to a disable configuration by connecting the at least one input capacitor to an input electrode.

5. The bio-signal amplifier of claim 1, wherein the parallel-RC circuit acts as an open-circuit to the first amplifier stage when the at least one RC resistor is greater than an output impedance of the first amplifier stage.

6. The bio-signal amplifier of claim 1, wherein, the parallel-RC circuit acts as a short circuit at the chopping frequency when the impedance of the at least one RC capacitor is less than an output impedance of the first amplifier stage.

7. The bio-signal amplifier of claim 1, wherein the parallel-RC circuit output is demodulated by the predetermined chopping frequency before being received by the second amplifier stage.

8. The bio-signal amplifier of claim 1, wherein the first output and the first input are connected by a first feedback loop comprising a first feedback resistor.

9. The bio-signal amplifier of claim 1, wherein the second output and the second input are connected by a second feedback loop comprising a second feedback resistor and a second feedback capacitor.

10. The bio-signal amplifier of claim 1, wherein the second output and the first input are connected by a third feedback loop comprising a third feedback capacitor.

11. The bio-signal amplifier of claim 2, wherein the second output and the first input are connected by a DC-servo feedback loop comprising an integrator that utilizes a duty-cycled resistor, wherein the duty-cycled resistor is connected in series to a DC-servo feedback switch configured to periodically remove the duty-cycled resistor from the DC-servo feedback loop.

12. The bio-signal amplifier of claim 5, wherein the at least one RC resistor is connected in series to a RC switch configured to periodically remove the at least one RC resistor from the RC circuit.

13. The bio-signal amplifier of claim 8, wherein the first feedback resistor is connected in series to a first feedback switch configured to periodically remove the first feedback resistor from the first feedback loop.

14. The bio-signal amplifier of claim 11, wherein the second output is connected to an anti-aliasing filter.

15. The bio-signal amplifier of claim 1, wherein the parallel-RC circuit does not include active circuit elements.

16. The bio-signal amplifier of claim 1, wherein the parallel-RC circuit adds nominal area to the amplifier's total area.

* * * * *